(12) United States Patent
Bebbington et al.

(10) Patent No.: US 7,091,343 B2
(45) Date of Patent: Aug. 15, 2006

(54) COMPOSITIONS USEFUL AS INHIBITORS OF PROTEIN KINASES

(75) Inventors: David Bebbington, Newbury (GB); Hayley Binch, Harwell (GB); Jean-Damien Charrier, Grove Wantage (GB); Simon Everitt, Bucks (GB); Julian M. C. Golec, Ashbury (GB); David Kay, Purton (GB); Ronald Knegtel, Abingdon (GB); Andrew Miller, Upton (GB); Francoise Pierard, Drayton (GB)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 3 days.

(21) Appl. No.: 10/389,296

(22) Filed: Mar. 14, 2003

(65) Prior Publication Data

US 2004/0009974 A1   Jan. 15, 2004

Related U.S. Application Data

(60) Provisional application No. 60/365,003, filed on Mar. 15, 2002.

(51) Int. Cl.
*C07D 403/12*  (2006.01)
*C07D 409/14*  (2006.01)
*C07D 417/14*  (2006.01)
*A61K 31/506*  (2006.01)
*A61P 35/00*   (2006.01)

(52) U.S. Cl. ............. 544/238; 544/295; 544/317; 544/324; 544/328; 514/252.05; 514/252.15; 514/255.05

(58) Field of Classification Search ........... 514/252.05, 514/252.15, 255.05, 256, 257; 544/238, 544/295, 317, 324, 328
See application file for complete search history.

(56) References Cited

U.S. PATENT DOCUMENTS

2002/0052386 A1*  5/2002  Armistead et al. .......... 514/269

FOREIGN PATENT DOCUMENTS

| WO | WO 01/60816 | 8/2001 |
|---|---|---|
| WO | WO 02/22601 | 3/2002 |
| WO | WO 02/50065 | 6/2002 |
| WO | WO 02/50066 | 6/2002 |

OTHER PUBLICATIONS

Eldar-Finkelman et al Expert Opinion on Investigational Drugs (Ashley Publications), 2003, vol. 12, No. 9, pp. 1511-1519.*
Alonso M, Martinez A., Curr Med Chem. Mar. 2004;11(6):755-63.*
Wagman AS, Johnson KW, Bussiere DE., Curr Pharm Des. 2004; 10(10):1105-37.*
Steven L. Warner, David J. Bearss, Haiyong Han and Daniel D. Von Hoff, Molecular Cancer Therapeutics, vol. 2, 589-595, Jun. 2003.*
Margaret C. Frame, Biochimica et Biophysica Acta-Reviews on Cancer, vol. 1602, Issue 2, Jun. 21, 2002, pp. 114-130.*

* cited by examiner

*Primary Examiner*—Thomas C. McKenzie
(74) *Attorney, Agent, or Firm*—Vertex Pharmaceuticals Incorporated

(57) ABSTRACT

The present invention relates to compounds useful of inhibitors of protein kinases. The invention also provides pharmaceutically acceptable compositions comprising said compounds and methods of using the compositions in the treatment of various disease, conditions, or disorders.

14 Claims, No Drawings

COMPOSITIONS USEFUL AS INHIBITORS OF PROTEIN KINASES

CROSS REFERENCE TO RELATED APPLICATION

This application claims priority to U.S. Provisional Patent Application 60/365,003 filed Mar. 15, 2002 the entirety of which is incorporated herein by reference.

TECHNICAL FIELD OF THE INVENTION

The present invention relates to compounds useful as inhibitors of protein kinases. The invention also provides pharmaceutically acceptable compositions comprising the compounds of the invention and methods of using the compositions in the treatment of, various disorders.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is protein kinases.

Protein kinases constitute a large family of structurally related enzymes that are responsible for the control of a variety of signal transduction processes within the cell. (See, Hardie, G. and Hanks, S. *The Protein Kinase Facts Book, I and II*, Academic Press, San Diego, Calif.: 1995). Protein kinases are thought to have evolved from a common ancestral gene due to the conservation of their structure and catalytic function. Almost all kinases contain a similar 250–300 amino acid catalytic domain. The kinases may be categorized into families by the substrates they phosphorylate (e.g., protein-tyrosine, protein-serine/threonine, lipids, etc.). Sequence motifs have been identified that generally correspond to each of these kinase families (See, for example, Hanks, S. K., Hunter, T., *FASEB J.* 1995, 9, 576–596; Knighton et al., *Science* 1991, 253, 407–414; Hiles et al., *Cell* 1992, 70, 419–429; Kunz et al., *Cell* 1993, 73, 585–596; Garcia-Bustos et al., *EMBO J.* 1994, 13, 2352–2361).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxin, and $H_2O_2$), cytokines (e.g., interleukin-1 (IL-1) and tumor necrosis factor α (TNF-α), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by protein kinase-mediated events as described above. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Accordingly, there has been a substantial effort in medicinal chemistry to find protein kinase inhibitors that are effective as therapeutic agents.

Aurora-2 is a serine/threonine protein kinase that has been implicated in human cancer, such as colon, breast and other solid tumors. This kinase is involved in protein phosphorylation events that regulate the cell cycle. Specifically, Aurora-2 plays a role in controlling the accurate segregation of chromosomes during mitosis. Misregulation of the cell cycle can lead to cellular proliferation and other abnormalities. In human colon cancer tissue, the Aurora-2 protein has been found to be overexpressed [Bischoff et al., *EMBO J.* 1998, 17, 3052–3065; Schumacher et al., *J. Cell Biol.* 1998, 143, 1635–1646; Kimura et al., *J. Biol. Chem.* 1997, 272, 13766–13771]. Thus, Aurora-2 inhibitors have an important role in the treatment of Aurora-2 mediated diseases.

Glycogen synthase kinase-3 (GSK-3) is a serine/threonine protein kinase comprised of α and β isoforms that are each encoded by distinct genes [Coghlan et al., *Chemistry & Biology* 2000, 7, 793–803; and Kim and Kimmel, *Curr. Opinion Genetics Dev.,* 2000 10, 508–514]. GSK-3 has been implicated in various diseases including diabetes, Alzheimer's disease, CNS disorders such as manic depressive disorder and neurodegenerative diseases, and cardiomyocyte hypertrophy [PCT Application Nos.: WO 99/65897 and WO 00/38675; and Haq et al., *J. Cell Biol.* 2000, 151, 117–130]. These diseases may be caused by, or result in, the abnormal operation of certain cell signaling pathways in which GSK-3 plays a role. GSK-3 has been found to phosphorylate and modulate the activity of a number of regulatory proteins. These proteins include glycogen synthase, which is the rate limiting enzyme necessary for glycogen synthesis, the microtubule associated protein Tau, the gene transcription factor β-catenin, the translation initiation factor e1F2B, as well as ATP citrate lyase, axin, heat shock factor-1, c-Jun, c-myc, c-myb, CREB, and CEPBα. These diverse protein targets implicate GSK-3 in many aspects of cellular metabolism, proliferation, differentiation, and development.

In a GSK-3 mediated pathway that is relevant for the treatment of type II diabetes, insulin-induced signaling leads to cellular glucose uptake and glycogen synthesis. Along this pathway, GSK-3 is a negative regulator of the insulin-induced signal. Normally, the presence of insulin causes inhibition of GSK-3 mediated phosphorylation and deactivation of glycogen synthase. The inhibition of GSK-3 leads to increased glycogen synthesis and glucose uptake [Klein et al., *PNAS* 1996, 93, 8455–8459; Cross et al., *Biochem. J.* 1994, 303, 21–26); Cohen, *Biochem. Soc. Trans.* 1993, 21, 555–567; and Massillon et al., *Biochem J.* 1994, 299, 123–128]. However, in a diabetic patient, where the insulin response is impaired, glycogen synthesis and glucose uptake fail to increase despite the presence of relatively high blood levels of insulin. This leads to abnormally high blood levels of glucose with acute and long-term effects that may ultimately result in cardiovascular disease, renal failure and blindness. In such patients, the normal insulin-induced inhibition of GSK-3 fails to occur. It has also been reported that in patients with type II diabetes, GSK-3 is overexpressed [see, PCT Application: WO 00/38675]. Therapeutic inhibitors of GSK-3 are therefore potentially useful for treating diabetic patients suffering from an impaired response to insulin.

GSK-3 activity has also been associated with Alzheimer's disease. This disease is characterized by the well-known β-amyloid peptide and the formation of intracellular neurofibrillary tangles. The neurofibrillary tangles contain hyperphosphorylated Tau protein, in which Tau is phosphorylated on abnormal sites. GSK-3 has been shown to phosphorylate these abnormal sites in cell and animal models. Furthermore, inhibition of GSK-3 has been shown to prevent hyperphosphorylation of Tau in cells [Lovestone et al., *Current Biology* 1994, 4, 1077–86; and Brownlees et al., *Neuroreport* 1997, 8, 3251–55]. Therefore, it is believed that GSK-3 activity may promote generation of the neurofibrillary tangles and the progression of Alzheimer's disease.

Another substrate of GSK-3 is β-catenin, which is degradated after phosphorylation by GSK-3. Reduced levels of β-catenin have been reported in schizophrenic patients and have also been associated with other diseases related to increase in neuronal cell death [Zhong et al., *Nature* 1998, 395, 698–702; Takashima et al., *PNAS* 1993, 90, 7789–93; and Pei et al., *J. Neuropathol. Exp* 1997, 56, 70–78].

GSK-3 activity has also been associated with stroke [Wang et al., *Brain Res* 2000, 859, 381–5; Sasaki et al., *Neurol Res* 2001, 23, 588–92; Hashimoto et al., *J. Biol. Chem* 2002, 277, 32985–32991].

Another kinase family of particular interest is the Src family of kinases. These kinases are implicated in cancer, immune system dysfunction and bone remodeling diseases. For general reviews, see Thomas and Brugge, *Annu. Rev. Cell Dev. Biol.* 1997, 13, 513; Lawrence and Niu, *Pharmacol. Ther.* 1998, 77, 81; Tatosyan and Mizenina, *Biochemistry* (Moscow) 2000, 65, 49–58; Boschelli et al., *Drugs of the Future* 2000, 25(7), 717.

Members of the Src family include the following eight kinases in mammals: Src, Fyn, Yes, Fgr, Lyn, Hck, Lck, and Blk. These are nonreceptor protein kinases that range in molecular mass from 52 to 62 kD. All are characterized by a common structural organization that is comprised of six distinct functional domains: Src homology domain 4 (SH4), a unique domain, SH3 domain, SH2 domain, a catalytic domain (SH1), and a C-terminal regulatory region. Tatosyan et al. *Biochemistry* (Moscow) 2000, 65, 49–58.

Based on published studies, Src kinases are considered as potential therapeutic targets for various human diseases. Mice that are deficient in Src develop osteopetrosis, or bone build-up, because of depressed bone resorption by osteoclasts. This suggests that osteoporosis resulting from abnormally high bone resorption can be treated by inhibiting Src. Soriano et al., *Cell* 1992, 69, 551 and Soriano et al., *Cell* 1991, 64, 693.

Suppression of arthritic bone destruction has been achieved by the overexpression of CSK in rheumatoid synoviocytes and osteoclasts. Takayanagi et al., *J. Clin. Invest.* 1999, 104, 137. CSK, or C-terminal Src kinase, phosphorylates and thereby inhibits Src catalytic activity. This implies that Src inhibition may prevent joint destruction that is characteristic in patients suffering from rheumatoid arthritis. Boschelli et al., *Drugs of the Future* 2000, 25(7), 717.

Src also plays a role in the replication of hepatitis B virus. The virally encoded transcription factor HBx activates Src in a step required for propagation of the virus. Klein et al., *EMBO J.* 1999, 18, 5019, and Klein et al., *Mol. Cell. Biol.* 1997, 17, 6427.

A number of studies have linked Src expression to cancers such as colon, breast, hepatic and pancreatic cancer, certain B-cell leukemias and lymphomas. Talamonti et al., *J. Clin. Invest.* 1993, 91, 53; Lutz et al., *Biochem. Biophys. Res.* 1998 243, 503; Rosen et al., *J. Biol. Chem.* 1986, 261, 13754; Bolen et al., *Proc. Natl. Acad. Sci. USA* 1987, 84, 2251; Masaki et al., *Hepatology* 1998, 27, 1257; Biscardi et al., *Adv. Cancer Res.* 1999, 76, 61; Lynch et al., *Leukemia* 1993, 7, 1416. Furthermore, antisense Src expressed in ovarian and colon tumor cells has been shown to inhibit tumor growth. Wiener et al., *Clin. Cancer Res.,* 1999, 5, 2164; Staley et al., *Cell Growth Diff.* 1997, 8, 269.

Accordingly, there is a great need to develop compounds useful as inhibitors of protein kinases. In particular, it would be desirable to develop compounds that are useful as inhibitors of Aurora-2, GSK-3, and Src particularly given the inadequate treatments currently available for the majority of the disorders implicated in their activation.

SUMMARY OF THE INVENTION

It has now been found that compounds of this invention, and pharmaceutically acceptable compositions thereof, are effective as inhibitors of protein kinases. In certain embodiments, these compounds are effective as inhibitors of Aurora-2, GSK-3, and Src protein kinases. These compounds have the general formula Ia and Ib:

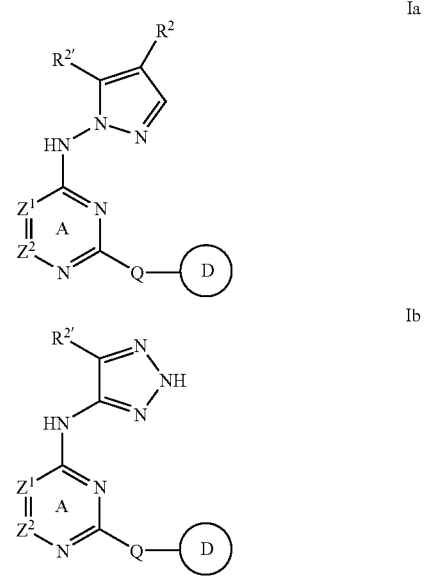

or a pharmaceutically acceptable derivative thereof, wherein $R^2$, $R^{2'}$, $Z^1$, $Z^2$, Q, and Ring D are as defined below.

These compounds and pharmaceutically acceptable compositions thereof are useful for treating or preventing a variety of diseases, disorders or conditions, including, but not limited to, heart disease, diabetes, Alzheimer's disease, immunodeficiency disorders, inflammatory diseases, allergic diseases, autoimmune diseases, destructive bone disorders such as osteoporosis, proliferative disorders, infectious diseases, immunologically-mediated diseases, neurodegenerative or neurological disorders, or viral diseases. The compositions are also useful in methods for preventing cell death and hyperplasia and therefore may be used to treat or prevent reperfusion/ischemia in stroke, heart attacks, and organ hypoxia. The compositions are also useful in methods for preventing thrombin-induced platelet aggregation.

The compounds provided by this invention are also useful for the study of kinases in biological and pathological phenomena; the study of intracellular signal transduction pathways mediated by such kinases; and the comparative evaluation of new kinase inhibitors.

DETAILED DESCRIPTION OF THE INVENTION

I. General Description of Compounds of the Invention:

The present invention relates to a compound of formula Ia and Ib:

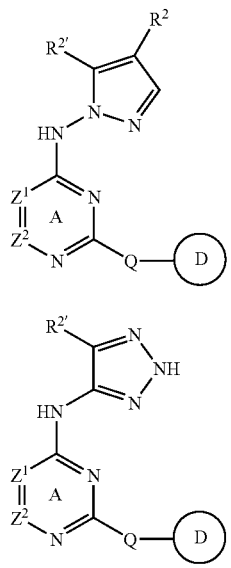

or a pharmaceutically acceptable derivative thereof, wherein:

$R^2$ is —R, oxo, halogen, —CN, —$NO_2$, —$CO_2R$, —Ar, -T-Ar, or -T-R;

$R^{2'}$ is R, or $R^2$ and $R^{2'}$ are taken together to form a optionally substituted 5–7 membered, partially unsaturated or fully unsaturated ring having zero to two ring heteroatoms independently selected from nitrogen, oxygen, or sulfur, wherein:

each substitutable ring nitrogen of the ring formed by $R^2$ and $R^{2'}$ is optionally substituted;

each occurrence of R is independently hydrogen, an optionally substituted $C_{1-6}$ aliphatic group, or Ar;

$Z^1$ is nitrogen or $CR^x$;

$R^x$ is —R, halogen, —$N(R)_2$, —$NO_2$, —CN, —$CO_2R$, —OR, or —SR; wherein two R bound to the same nitrogen atom may be taken together with that nitrogen atom to form a five or six membered heterocyclic or heteroaryl ring having one to two additional heteratoms independently selected from oxygen, nitrogen, or sulfur;

$Z^2$ is nitrogen or $CR^y$, provided that $Z^1$ and $Z^2$ are not simultaneously nitrogen;

$R^y$ is —$R^1$, —CN, halogen, —$NO_2$, —Ar, -T-Ar, or -T-R, or $R^x$ and $R^y$ are taken together to form an optionally substituted 5–7 membered partially unsaturated or fully unsaturated ring having zero to two heteroatoms independently selected from oxygen, sulfur, or nitrogen, wherein:

each substitutable ring nitrogen of the ring formed by $R^x$ and $R^y$ is optionally substituted;

$R^1$ is hydrogen or an optionally substituted $C_{1-6}$ aliphatic group;

each Ar is independently an optionally substituted 3–6 membered heterocyclic ring having one or two heteroatoms independently selected from nitrogen, oxygen, or sulfur; or a 5 or 6 membered aryl ring having zero to three heteroatoms independently selected from nitrogen, oxygen, or sulfur, wherein:

Ar is optionally fused to a five or six membered partially unsaturated, or fully unsaturated ring having zero to two heteroatoms independently selected from nitrogen, oxygen, or sulfur;

T is a $C_{1-4}$ alkylidene chain wherein one methylene unit of T is optionally replaced by —O—, —S—, —C(O)—, —$CO_2$—, —NR—, —NRC(O)—, —NRC(O)NR—, —C(O)C(O)—, —OC(O)NR—, —$NRCO_2$—, —$SO_2NR$—, —$NRSO_2$—, or —$NRSO_2NR$—;

Q is —N(R')—, —S—, —O—, —$C(R')_2$—, or a valence bond, provided that Q is other than a valence bond when Ht is a triazole ring; wherein each R' is independently hydrogen or $C_{1-6}$ aliphatic; and Ring D is a 5 or 6 membered optionally substituted monocyclic aryl ring having zero to two heteroatoms independently selected from nitrogen, oxygen, or sulfur; or an eight to ten membered partially unsaturated or fully unsaturated bicyclic ring having zero to four heteroatoms independently selected from nitrogen, oxygen, or sulfur.

2. Compounds and Definitions:

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1–20 aliphatic carbon atoms. In some embodiments, aliphatic groups contain 1–10 aliphatic carbon atoms. In other embodiments, aliphatic groups contain 1–8 aliphatic carbon atoms. In still other embodiments, aliphatic groups contain 1–6 aliphatic carbon atoms, and in yet other embodiments aliphatic groups contain 1–4 aliphatic carbon atoms. In some embodiments, "cycloaliphatic" (or "carbocycle" or "cycloalkyl") refers to a monocyclic $C_3$–$C_8$ hydrocarbon or bicyclic $C_8$–$C_{12}$ hydrocarbon that is completely saturated or that contains one or more units of unsaturation, but which is not aromatic, that has a single point of attachment to the rest of the molecule wherein any individual ring in said bicyclic ring system has 3–7 members. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "heteroaliphatic", as used herein, means aliphatic groups wherein one or two carbon atoms are independently replaced by one or more of oxygen, sulfur, nitrogen, phosphorus, or silicon. Heteroaliphatic groups may be substituted or unsubstituted, branched or unbranched, cyclic or acyclic, and include "heterocycle", "heterocyclyl", "heterocycloaliphatic", or "heterocyclic" groups.

The term "heterocycle", "heterocyclyl", "heterocycloaliphatic", or "heterocyclic" as used herein means non-aromatic, monocyclic, bicyclic, or tricyclic ring systems in which one or more ring members is an independently selected heteroatom. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl or heteroaryl group are selected from halogen; —R°; —OR°; —SR°; 1,2-methylene-dioxy; 1,2-ethylenedioxy; phenyl (Ph) optionally substituted with R°; —O(Ph) optionally substituted with R°; —$(CH_2)_{1-2}$(Ph), optionally substituted with R°; —CH=CH(Ph), optionally substituted with R°; —$NO_2$; —CN; —N(R°)$_2$; —NR°C(O)R°; —NR°C(S)R°; —NR°C(O)N(R°)$_2$; —NR°C(S)N(R°)$_2$; —NR°CO$_2$R°; —NR°NR°C(O)R°; —NR°NR°C(O)N(R°)$_2$; —NR°NR°CO$_2$R°; —C(O)C(O)R°; —C(O)CH$_2$C(O)R°; —CO$_2$R°; —OC(O)R°; —C(O)R°; —C(S)R°; —C(O)N(R°)$_2$; —OC(O)N(R°)$_2$; —C(NOR°)R°; —S(O)R°; —S(O)$_2$R°; —S(O)$_3$R°; —SO$_2$N(R°)$_2$; —NR°SO$_2$N(R°)$_2$; —NR°SO$_2$R°; —N(OR°)R°; —C(=S)N(R°)$_2$; —C(=NH)—N(R°)$_2$; or —$(CH_2)_{0-2}$NHC(O)R° wherein each independent occurrence of R° is selected from hydrogen, optionally substituted $C_{1-6}$ aliphatic, an unsubstituted 5–6 membered heteroaryl or heterocyclic ring, phenyl, —O(Ph), or —$CH_2$(Ph), or, notwithstanding the definition above, two independent occurrences of R°, on the same substituent or different substituents, taken together with the atom(s) to which each R° group is bound, form a 3–8-membered cycloalkyl, heterocyclyl, aryl, or heteroaryl ring having 0–3 heteroatoms independently selected from nitrogen, oxygen, or sulfur. Optional substituents on the aliphatic group of R° are selected from $NH_2$, NH($C_{1-4}$aliphatic), N($C_{1-4}$aliphatic)$_2$, halogen, $C_{1-4}$aliphatic, OH, O($C_{1-4}$aliphatic), $NO_2$, CN, $CO_2$H, $CO_2$($C_{1-4}$aliphatic), O(halo$C_{1-4}$aliphatic), or halo$C_{1-4}$aliphatic, wherein each of the foregoing $C_{1-4}$aliphatic groups of R° is unsubstituted.

An aliphatic or heteroaliphatic group, or a non-aromatic heterocyclic ring may contain one or more substituents. Suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)$_2$, =NNHC(O)R*, =NNHCO$_2$(alkyl), =NNHSO$_2$(alkyl), or =NR*, where each R* is independently selected from hydrogen or an optionally substituted $C_{1-6}$ aliphatic. Optional substituents on the aliphatic group of R* are selected from $NH_2$, NH($C_{1-4}$ aliphatic), N($C_{1-4}$ aliphatic)$_2$, halogen, $C_{1-4}$ aliphatic, OH, O($C_{1-4}$ aliphatic), $NO_2$, CN, $CO_2H$, $CO_2$($C_{1-4}$ aliphatic), O(halo $C_{1-4}$ aliphatic), or halo ($C_{1-4}$ aliphatic), wherein each of the foregoing $C_{1-4}$ aliphatic groups of R* unsubstituted.

Optional substituents on the nitrogen of a non-aromatic heterocyclic ring are selected from —$R^+$, —N($R^+$)$_2$, —C(O)$R^+$, —CO$_2R^+$, —C(O)C(O)$R^+$, —C(O)CH$_2$C(O)$R^+$, —SO$_2R^+$, —SO$_2$N($R^+$)$_2$, —C(=S)N($R^+$)$_2$, —C(=NH)—N($R^+$)$_2$, or —NR$^+$SO$_2R^+$; wherein $R^+$ is hydrogen, an optionally substituted $C_{1-6}$ aliphatic, optionally substituted phenyl, optionally substituted —O(Ph), optionally substituted —CH$_2$(Ph), optionally substituted —(CH$_2$)$_{1-2}$(Ph); optionally substituted —CH=CH(Ph); or an unsubstituted 5–6 membered heteroaryl or heterocyclic ring having one to four heteroatoms independently selected from oxygen, nitrogen, or sulfur, or, notwithstanding the definition above, two independent occurrences of $R^+$, on the same substituent or different substituents, taken together with the atom(s) to which each $R^+$ group is bound, form a 3–8-membered cycloalkyl, heterocyclyl, aryl, or heteroaryl ring having 0–3 heteroatoms independently selected from nitrogen, oxygen, or sulfur. Optional substituents on the aliphatic group or the phenyl ring of $R^+$ are selected from NH$_2$, NH($C_{1-4}$ aliphatic), N($C_{1-4}$ aliphatic)$_2$, halogen, $C_{1-4}$ aliphatic, OH, O($C_{1-4}$ aliphatic), NO$_2$, CN, CO$_2$H, CO$_2$($C_{1-4}$ aliphatic), O(halo $C_{1-4}$ aliphatic), or halo($C_{1-4}$ aliphatic), wherein each of the foregoing $C_{1-4}$ aliphatic groups of $R^+$ is unsubstituted.

The term "alkylidene chain" refers to a straight or branched carbon chain that may be fully saturated or have one or more units of unsaturation and has two points of attachment to the rest of the molecule.

As detailed above, in some embodiments, two independent occurrences of R° (or $R^+$, or any other variable similarly defined herein), are taken together together with the atom(s) to which each variable is bound to form a 3–8-membered cycloalkyl, heterocyclyl, aryl, or heteroaryl ring having 0–3 heteroatoms independently selected from nitrogen, oxygen, or sulfur. Exemplary rings that are formed when two independent occurrences of R° (or $R^+$, or any other variable similarly defined herein) are taken together with the atom(s) to which each variable is bound include, but are not limited to the following: a) two independent occurrences of R° (or $R^+$, or any other variable similarly defined herein) that are bound to the same atom and are taken together with that atom to form a ring, for example, N(R°)$_2$, where both occurrences of R° are taken together with the nitrogen atom to form a piperidin-1-yl, piperazin-1-yl, or morpholin-4-yl group; and b) two independent occurrences of R° (or $R^+$, or any other variable similarly defined herein) that are bound to different atoms and are taken together with both of those atoms to form a ring, for example where a phenyl group is substituted with two occurrences of

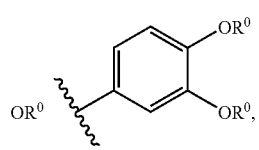

these two occurrences of R° are taken together with the oxygen atoms to which they are bound to form a fused 6-membered oxygen containing ring:

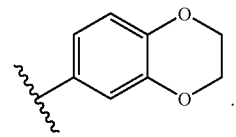

It will be appreciated that a variety of other rings can be formed when two independent occurrences of R° (or $R^+$, or any other variable similarly defined herein) are taken together with the atom(s) to which each variable is bound and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

3. Description of Exemplary Compounds:

According to one embodiment, the present invention relates to a compound of formula Ia or Ib:

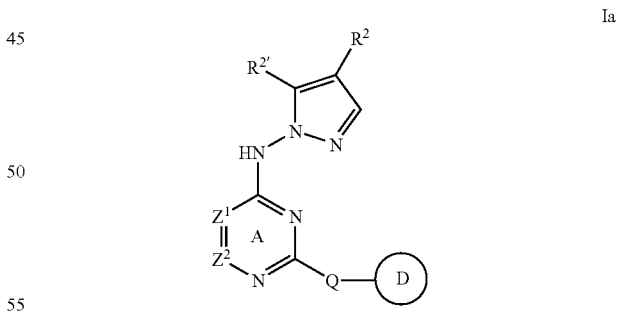

Ia

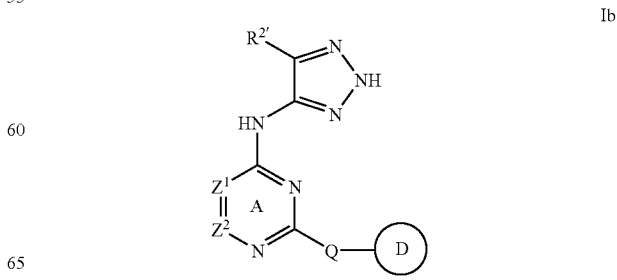

Ib or a pharmaceutically acceptable derivative thereof, wherein:

$R^2$ is —R, oxo, halogen, —CN, —$NO_2$, —$CO_2R$, —Ar, -T-Ar, or -T-R;

$R^{2'}$ is R, or $R^2$ and $R^{2'}$ are taken together to form a optionally substituted 5–7 membered, partially unsaturated or fully unsaturated ring having zero to two ring heteroatoms independently selected from nitrogen, oxygen, or sulfur, wherein:
   each substitutable ring nitrogen of the ring formed by $R^2$ and $R^{2'}$ is optionally substituted;

each occurrence of R is independently hydrogen, an optionally substituted $C_{1-6}$ aliphatic group, or Ar;

$Z^1$ is nitrogen or $CR^x$;

$R^x$ is —R, halogen, —$N(R)_2$, —$NO_2$, —CN, —$CO_2R$, —OR, or —SR; wherein
   two R bound to the same nitrogen atom may be taken together with that nitrogen atom to form a five or six membered heterocyclic or heteroaryl ring having one to two additional heteratoms independently selected from oxygen, nitrogen, or sulfur;

$Z^2$ is nitrogen or $CR^y$, provided that $Z^1$ and $Z^2$ are not simultaneously nitrogen;

$R^y$ is —$R^1$, —CN, halogen, —$NO_2$, —Ar, -T-Ar, or -T-R, or $R^x$ and $R^y$ are taken together to form an optionally substituted 5–7 membered partially unsaturated or fully unsaturated ring having zero to two heteroatoms independently selected from oxygen, sulfur, or nitrogen, wherein:
   each substitutable ring nitrogen of the ring formed by $R^x$ and $R^y$ is optionally substituted;

$R^1$ is hydrogen or an optionally substituted $C_{1-6}$ aliphatic group;

each Ar is independently an optionally substituted 3–6 membered heterocyclic ring having one or two heteroatoms independently selected from nitrogen, oxygen, or sulfur; or a 5 or 6 membered aryl ring having zero to three heteroatoms independently selected from nitrogen, oxygen, or sulfur, wherein:
   Ar is optionally fused to a five or six membered partially unsaturated, or fully unsaturated ring having zero to two heteroatoms independently selected from nitrogen, oxygen, or sulfur;

T is a $C_{1-4}$ alkylidene chain wherein one methylene unit of T is optionally replaced by —O—, —S—, —C(O)—, —$CO_2$—, —NR—, —NRC(O)—, —NRC(O)NR—, —C(O)C(O)—, —OC(O)NR—, —$NRCO_2$—, —$SO_2NR$—, —$NRSO_2$—, or —$NRSO_2NR$—;

Q is —N(R')—, —S—, —O—, —C(R')$_2$—, or a valence bond, provided that Q is other than a valence bond when Ht is a triazole ring; wherein
   each R' is independently hydrogen or $C_{1-6}$ aliphatic; and Ring D is a 5 or 6 membered optionally substituted monocyclic aryl ring having zero to two heteroatoms independently selected from nitrogen, oxygen, or sulfur; or an eight to ten membered partially unsaturated or fully unsaturated bicyclic ring having zero to four heteroatoms independently selected from nitrogen, oxygen, or sulfur.

According to another embodiment, the present invention relates to a compound of formula Ia or Ib wherein:

$R^2$ is —R, halogen, —CN, —$NO_2$, —Ar, -T-Ar, or -T-R;

$R^{2'}$ is —R, or $R^2$ and $R^{2'}$ are taken together to form a five to seven membered, partially unsaturated or fully unsaturated ring having zero to two ring heteroatoms independently selected from nitrogen, oxygen, or sulfur, wherein:
   each substitutable ring nitrogen of the ring formed by $R^2$ and $R^{2'}$ is optionally and independently substituted by —R, —C(O)R, —$CO_2R$, —$SO_2R$, —$C(O)N(R)_2$ or —$SO_2N(R)_2$, and
   one to three substitutable ring carbons of the ring formed by $R^2$ and $R^{2'}$ are optionally and independently substituted with —R, —OR, —$N(R)_2$, —SR, —$NO_2$, —CN or halogen;

each occurrence of R is independently hydrogen, $C_{1-6}$ aliphatic, or Ar; wherein
   R is optionally substituted with one to three groups independently selected from oxo, —$CO_2R'$, —Ar, —OR', —$N(R')_2$, —SR', —$NO_2$, halogen, or —CN; wherein
      each R' is independently hydrogen or $C_{1-6}$ aliphatic, or two R' bound to the same nitrogen atom may be taken together with that nitrogen atom to form a five or six membered heterocyclic or heteroaryl ring having one to two additional heteroatoms independently selected from oxygen, nitrogen, or sulfur;

$Z^1$ is nitrogen or $CR^x$;

$R^x$ is —R, halogen, —$N(R)_2$, —$NO_2$, —CN, —$CO_2R$, —OR, or —SR; wherein
   two R bound to the same nitrogen atom may be taken together with that nitrogen atom to form a five or six membered heterocyclic or heteroaryl ring having one to two additional heteratoms independently selected from oxygen, nitrogen, or sulfur;

$Z^2$ is nitrogen or $CR^y$, provided that $Z^1$ and $Z^2$ are not simultaneously nitrogen;

$R^y$ is —$R^1$, —CN, halogen, —$NO_2$, —Ar, -T-Ar, or -T-R, or $R^x$ and $R^y$ are taken together to form a five to seven membered partially unsaturated or fully unsaturated ring having zero to two heteroatoms independently selected from oxygen, sulfur, or nitrogen, wherein:
   each substitutable ring nitrogen of the ring formed by $R^x$ and $R^y$ is optionally and independently substituted by —R, —C(O)R, —$CO_2R$, —$SO_2R$, —$C(O)N(R)_2$ or —$SO_2N(R)_2$, and
   one to three substitutable ring carbons of the ring formed by $R^x$ and $R^y$ are optionally and independently substituted with —R, —OR, —$N(R)_2$, —SR, —$NO_2$, —CN or halogen;

$R^1$ is hydrogen or a $C_{1-6}$ aliphatic optionally substituted with one to three groups independently selected from oxo, —$CO_2R'$, phenyl, —OR', —$N(R')_2$, —SR', —$NO_2$, halogen, or —CN;

each Ar is independently a three to six membered heterocyclic ring having one or two heteroatoms independently selected from nitrogen, oxygen, or sulfur; or a five or six membered aryl ring having zero to three heteroatoms independently selected from nitrogen, oxygen, or sulfur, wherein:
   Ar is optionally fused to a five or six membered partially unsaturated, or fully unsaturated ring having zero to two heteroatoms independently selected from nitrogen, oxygen, or sulfur; and wherein:
   Ar is optionally substituted with one to three groups independently selected from —R, —OR, —SR, —CN, —$NO_2$, oxo, halogen, —$N(R)_2$, —C(O)R, —OC(O)R, —CO₂R, —SO₂R, —SO₂N(R)₂, —N(R)SO₂R, —C(O)N(R), —C(O)N(R)₂, —OC(O)N(R), —OC(O)N(R)₂, —N(R)C(O)R, —N(R)C(O)N(R)₂, or —N(R)CO₂(R); and T is a $C_{1-4}$ alkylidene chain wherein one methylene unit of T is optionally replaced by —O—, —S—, —C(O)—, —CO₂—, —NR—, —NRC(O)—, —NRC(O)NR—, —C(O)C(O)—, —OC(O)NR—, —NRCO₂—, —SO₂NR—, —NRSO₂—, or —NRSO₂NR—;

Q is —N(R')—, —S—, —O—, —C(R')₂—, or a valence bond; and

Ring D is a five or six membered monocyclic aryl ring having zero to two heteroatoms independently selected from nitrogen, oxygen, or sulfur; or an eight to ten membered partially unsaturated or fully unsaturated bicyclic ring having zero to four heteroatoms independently selected from nitrogen, oxygen, or sulfur, wherein:

Ring D is optionally substituted with one to three substituents independently selected from —R, -T-R, -T-Ar, halogen, —CN, —NO₂, or —Ar.

$R^2$ and $R^{2'}$ of formula Ia may be taken together to form a ring ("$R^2/R^{2'}$ ring") fused to the pyrazole ring, thus providing a bicyclic ring system. Preferred $R^2/R^{2'}$ rings are optionally substituted five to seven membered, unsaturated or partially unsaturated rings having zero to two ring heteroatoms. Preferred $R^2/R^{2'}$ bicyclic ring systems include benzo, pyrido, and cyclohexo.

$R^x$ and $R^y$, when present in formula Ia and formula Ib, may be taken together to form a ring ("$R^x/R^y$ ring") fused to Ring A, thus providing a bicyclic ring system. Preferred $R^x/R^y$ rings are optionally substituted five or six membered unsaturated or partially unsaturated rings having zero to two heteroatoms. Preferred bicyclic ring systems containing Ring A are moieties I-A through I-AA shown below, wherein each substitutable carbon atom of the bicyclic ring systems is optionally and independently substituted with —R, —OR, —N(R)₂, —SR, —NO₂, —CN or halogen and wherein each substitutable ring nitrogen of the bicyclic ring systems is optionally and independently substituted with —R, —C(O)R, —CO₂R, —SO₂R, —C(O)N(R)₂ or —SO₂N(R)₂.

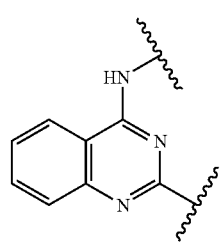

I-A

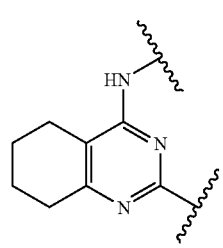

I-B

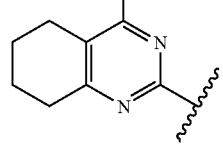

-continued

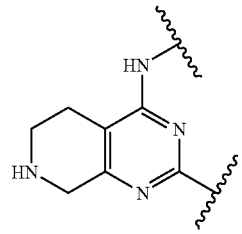

I-C

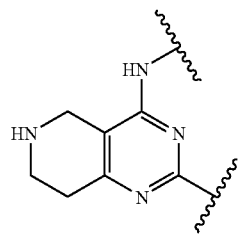

I-D

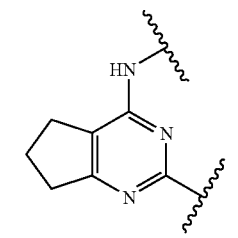

I-E

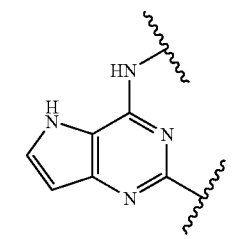

I-F

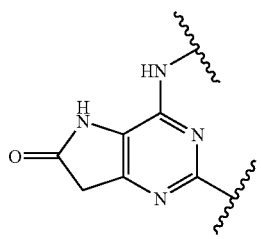

I-G

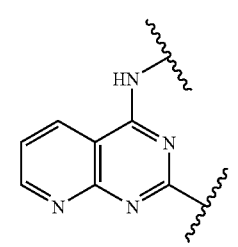

I-H

-continued
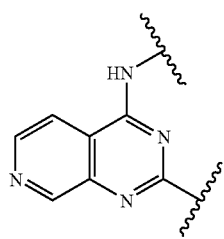
I-I
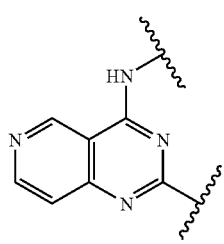
I-J
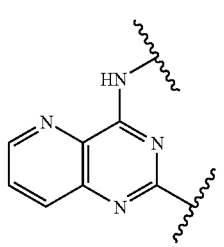
I-K
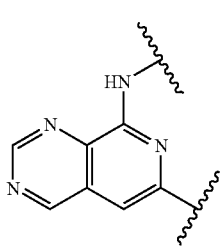
I-L
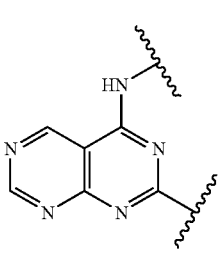
I-M
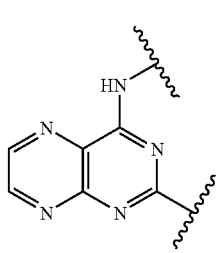
I-N
-continued
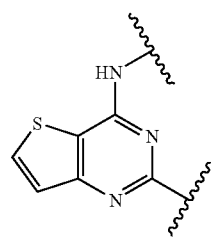
I-O
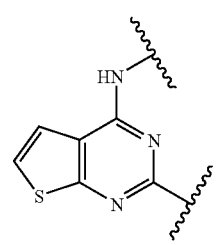
I-P
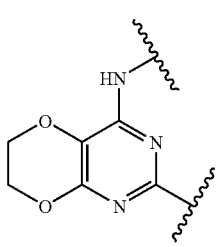
I-Q
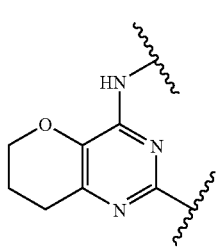
I-R
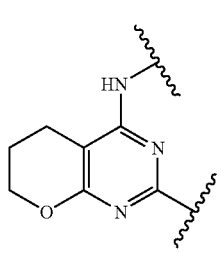
I-S
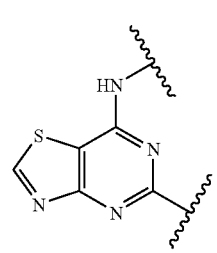
I-T -continued

I-U

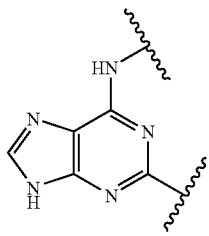

I-V

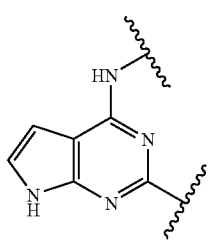

I-W

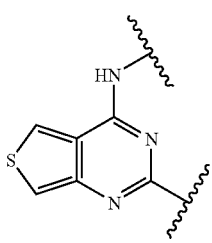

I-X

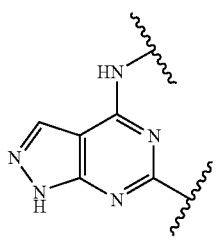

I-Y

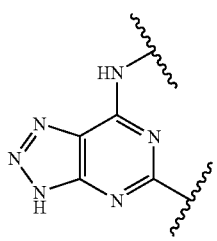

I-Z

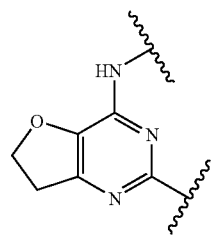

-continued

I-AA

[structure: fused bicyclic with HN-, N, O ring — 4,5-dihydrofuro[2,3-d]pyrimidine]

More preferred bicyclic Ring A systems are I-A, I-B, I-C, I-D, I-E, I-H, I-I, I-J, I-O, I-P, I-T, or I-U, even more preferably I-A, I-B, I-D, I-I, I-O, or I-U, and most preferably I-A, I-B, I-C, I-D, or I-I.

In the bicyclic Ring A system of formula Ia and formula Ib, the ring formed when $R^x$ and $R^y$ are taken together may be substituted or unsubstituted. Preferred substituents on the ring formed by $R^x$ and $R^y$ are halo, —R, —OR, —CN, —N(R)$_2$ or —NO$_2$. More preferred $R^x/R^y$ ring substituents are halo, —OR, or —N(R)$_2$, wherein R is hydrogen or $C_{1-4}$ aliphatic.

In the monocyclic Ring A system of formula Ia and formula Ib, (ie., wherein $R^x$ and $R^y$ do not form a ring), preferred $R^x$ groups, when present, are hydrogen, —N(R)$_2$, —OR, or a $C_{1-4}$ aliphatic group such as methyl, ethyl, cyclopropyl, or isopropyl. Preferred $R^y$ groups, when present, are —R$^1$, —Ar, -T-R, or -T-Ar wherein T is —NR—, —O—, or —S—. More preferred $R^y$ groups are $C_{1-4}$ aliphatic, T-$C_{1-4}$ aliphatic, five or six membered heteroaryl or heterocyclyl rings, or optionally substituted phenyl. The most preferred $R^y$ groups are methyl, ethyl, cyclopropyl, isopropyl, t-butyl, methoxyethylamino, methoxymethyl, methylamino, dimethylamino, dimethylaminopropyloxy, acetamido, 2-pyridyl, 3-pyridyl, 4-pyridyl, pyrrolidinyl, imidazolyl, furanyl, thiazolyl, thienyl, piperidinyl, morpholinyl, thiomorpholinyl, piperazinyl, or halo-substituted phenyl.

Preferred Q groups of formula Ia and formula Ib are —N(R')—, —S—, or a valence bond. More preferred Q groups of formula Ia and formula Ib are —N(R')— or —S—.

Preferred Ring D of formula Ia and formula Ib are an optionally substituted six membered monocyclic aryl ring having zero to two nitrogens or an optionally substituted nine or ten membered partially unsaturated or fully unsaturated bicyclic ring having zero to three heteroatoms independently selected from nitrogen, oxygen, or sulfur. More preferred Ring D groups of formula Ia and formula Ib are phenyl, imidazolyl, pyrazoloyl, pyridyl, pyridazinyl, pyrimidinyl, pyrazinyl, naphthyl, tetrahydronaphthyl, benzimidazolyl, benzthiazolyl, quinolinyl, quinazolinyl, benzodioxinyl, isobenzofuran, indanyl, indolyl, indolinyl, indazolyl, or isoquinolinyl.

On Ring D of formula Ia and formula Ib, preferred substituents are independently halo, —CN, —NO$_2$, or -T-R, wherein R is hydrogen or $C_{1-4}$ aliphatic. Preferred T-R substituents on Ring D are —C(O)R, —CO$_2$R, —C(O)NHR, —NHC(O)R, —N(R)$_2$, —NHSO$_2$R, —NHC(O)RN(R)$_2$, or —NHC(O)RNCO$_2$R. Most preferred substituents on Ring D of formula Ia and formula Ib are independently —Cl, —Br, —F, —CN, —CF₃, —CO₂H, —CONHMe, —CONHEt, —NH₂, —NHAc, —NHSO₂Me, —NHSO₂Et, —NHSO₂(n-propyl), —NHSO₂(isopropyl), —NHCOEt, —NHCOCH₂NHCH₃, —NHCOCH₂N(CO₂t-Bu)CH₃, —NHCOCH₂N(CH₃)₂, —NHCOCH₂CH₂N(CH₃)₂, —NHCOCH₂CH₂CH₂N(CH₃)₂, —NHCO(cyclopropyl), —NHCO(isopropyl), —NHCO(isobutyl), —NHCOCH₂(morpholin-4-yl), —NHCOCH₂CH₂(morpholin-4-yl), —NHCOCH₂CH₂CH₂(morpholin-4-yl), —NHCO₂(t-butyl), —NH(cyclohexyl), —NHMe, —NMe₂, —OH, —OMe, methyl, ethyl, cyclopropyl, isopropyl, or t-butyl.

Another embodiment relates to compounds of formula Ia and formula Ib wherein Q is a valence bond and Ring D has one substituent in the ortho position and optionally one or two additional substituents. When Q is a valence bond and Ring D has an ortho substituent, preferred ortho substituents on Ring D are —CN, —CF₃ or —Cl.

A preferred embodiment of the present invention is a compound of either formula IIa or formula IIb:

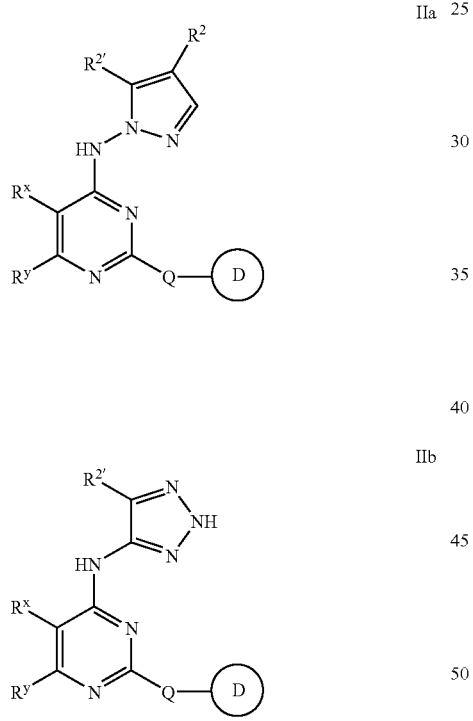

or a pharmaceutically acceptable salt thereof, wherein $R^x$, $R^y$, $R^{2'}$, $R^2$, Q, Ring D, and subcomponents thereof are as defined above for a compound of either formula Ia or formula Ib.

Preferred $R^2$, $R^{2'}$ (including embodiments where $R^2$ and $R^{2'}$ are taken together to form a ring), $R^x$, $R^y$ (including embodiments where $R^x$ and $R^y$ are taken together to form a ring), Q, and Ring D groups are as described above for compounds of formula Ia and formula Ib.

Representative compounds of formula IIa and formula IIb are shown below in Tables 2a and 2b.

TABLE 2a

Compounds of Formula IIa

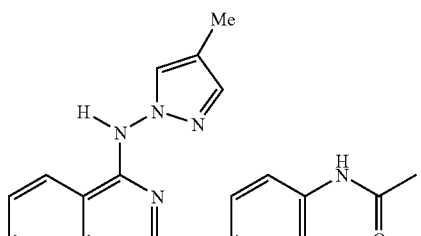

IIa-1

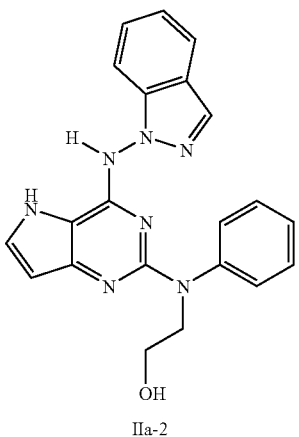

IIa-2

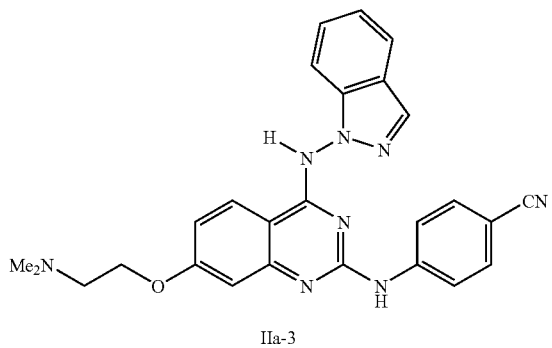

IIa-3

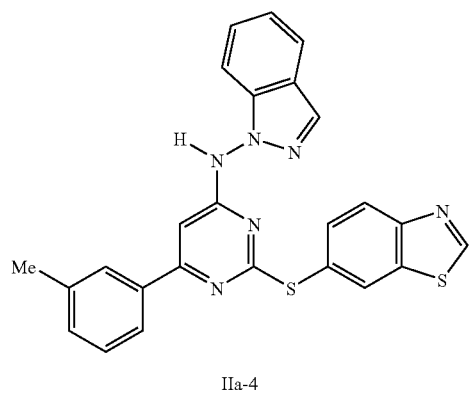

IIa-4

TABLE 2a-continued
Compounds of Formula IIa
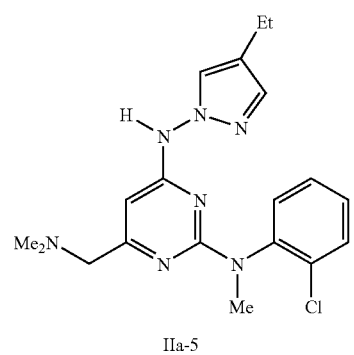
IIa-5
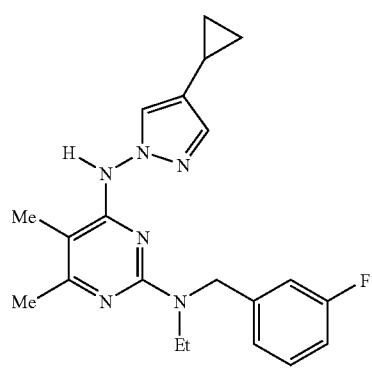
IIa-6
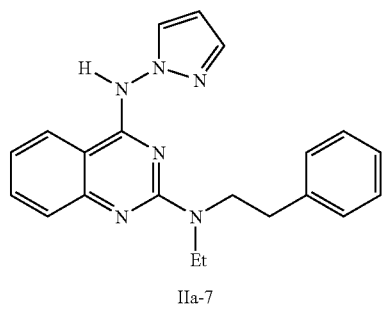
IIa-7
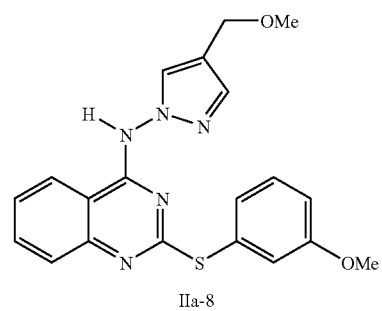
IIa-8
TABLE 2a-continued
Compounds of Formula IIa
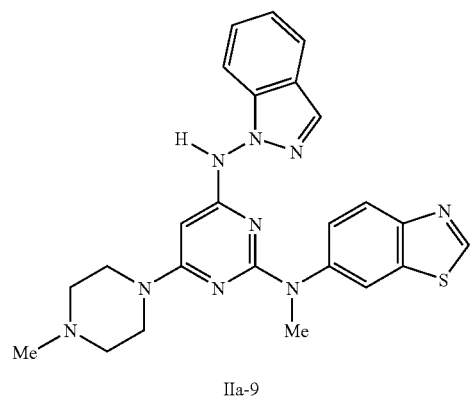
IIa-9
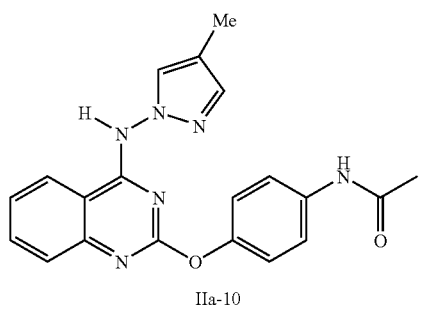
IIa-10
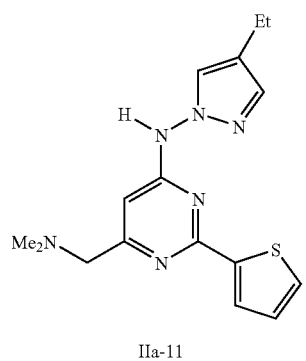
IIa-11
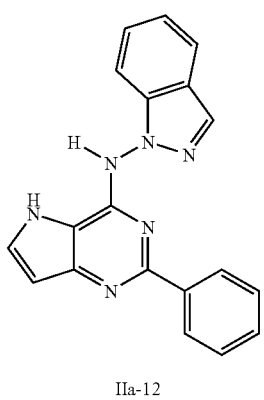
IIa-12

TABLE 2a-continued
Compounds of Formula IIa
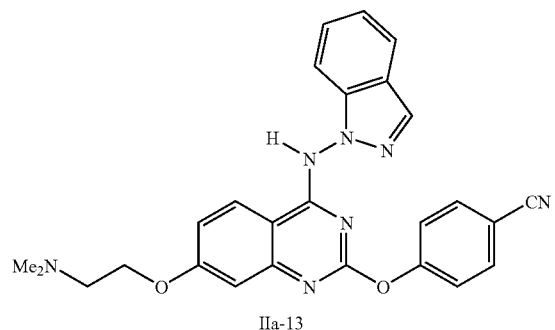
IIa-13
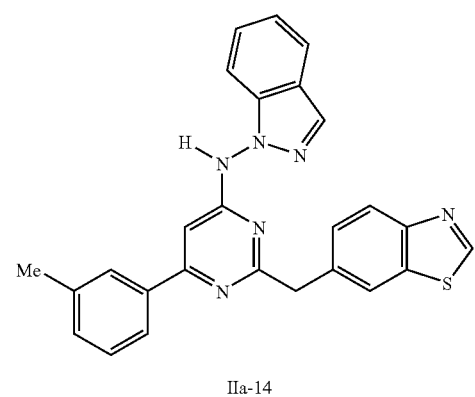
IIa-14
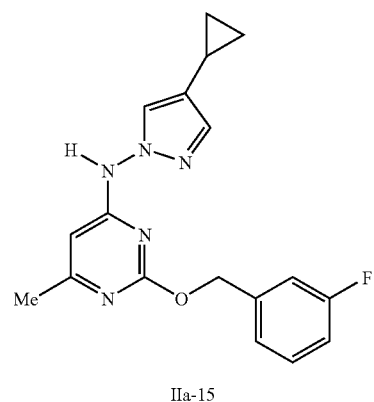
IIa-15
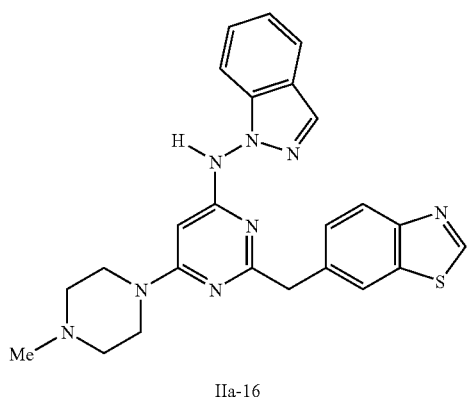
IIa-16
TABLE 2a-continued
Compounds of Formula IIa
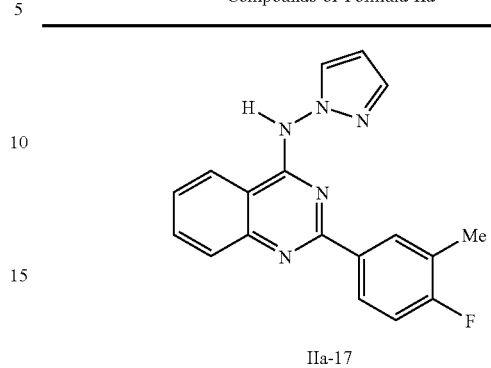
IIa-17
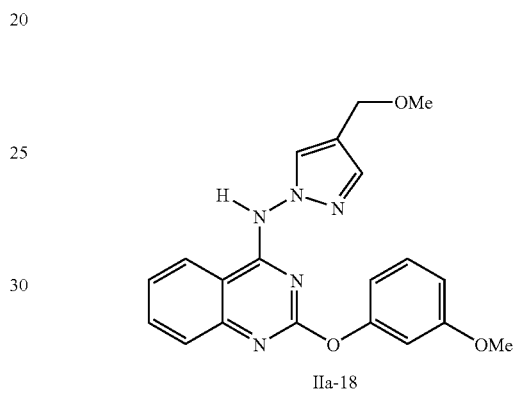
IIa-18
TABLE 2b
Compounds of Formula IIb
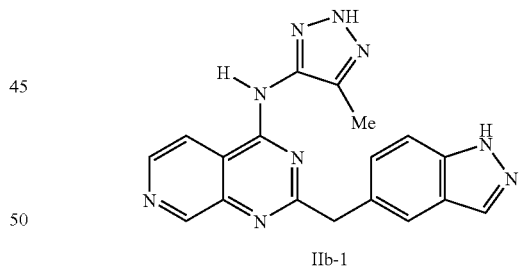
IIb-1
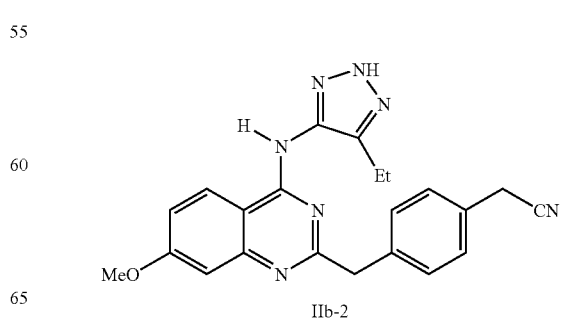
IIb-2

TABLE 2b-continued

Compounds of Formula IIb

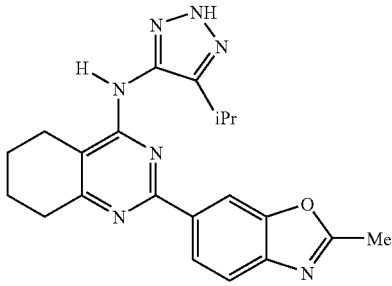

IIb-3

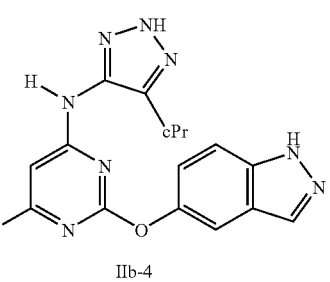

IIb-4

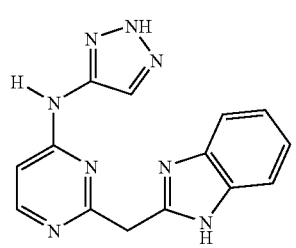

IIb-5

According to yet another embodiment the present invention relates to compounds of formula IIIa and formula IIIb:

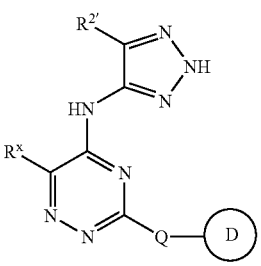

IIIa

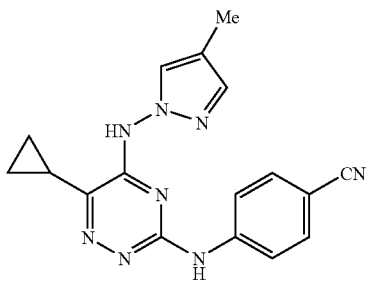

IIIb or a pharmaceutically acceptable salt thereof, wherein $R^x$, $R^{2'}$, $R^2$, Q, Ring D, and subcomponents thereof are as defined above for a compound of Formula Ia and Formula Ib.

Preferred $R^2$, $R^{2'}$ (including embodiments where $R^2$ and $R^{2'}$ are taken together to form a ring), $R^x$, Q, and Ring D groups are as described above for compounds of formula Ia and formula Ib.

Representative compounds of formula IIIa and formula IIIb are shown below in Tables 3a and 3b.

TABLE 3a

Compounds of Formula IIIa

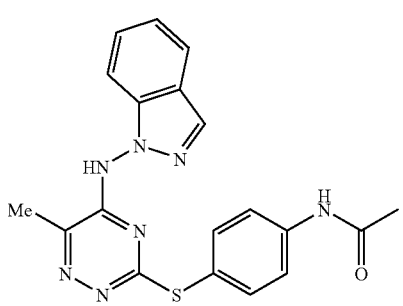

IIIa-1

IIIa-2

TABLE 3a-continued
Compounds of Formula IIIa
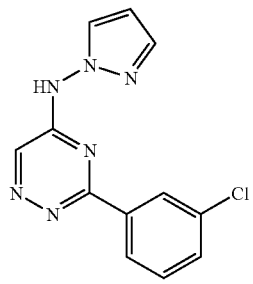
IIIa-3
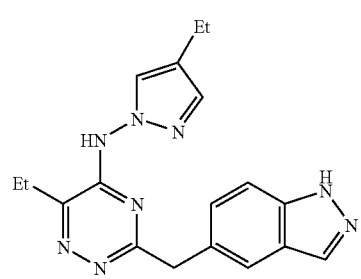
IIIa-4
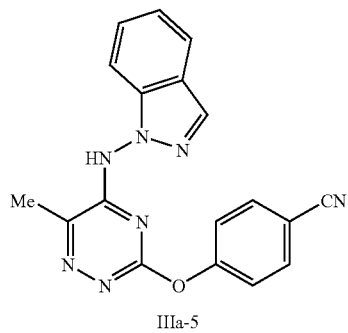
IIIa-5
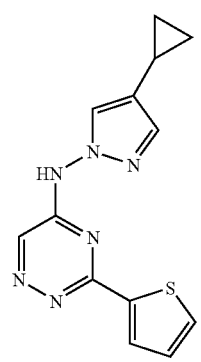
IIIa-6
TABLE 3b
Compounds of Formula IIIb
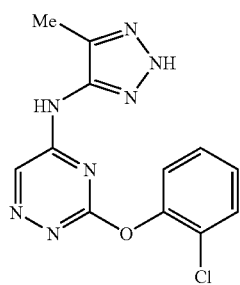
IIIb-1
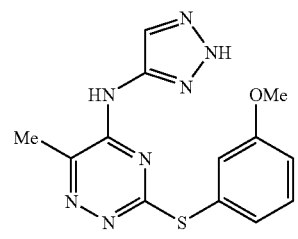
IIIb-2
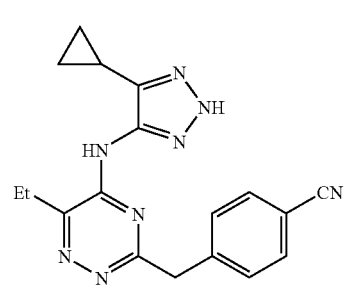
IIIb-3
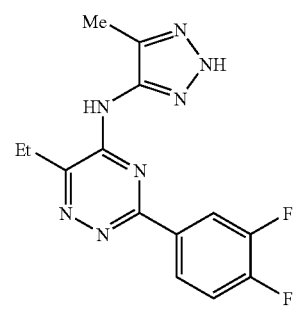
IIIb-4

TABLE 3b-continued

Compounds of Formula IIIb

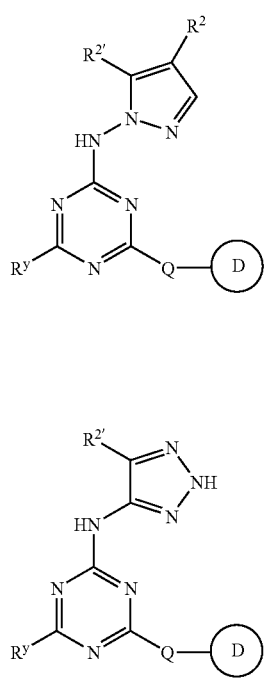

IIIb-5

According to yet another embodiment the present invention relates to compounds of formula IVa and formula IVb:

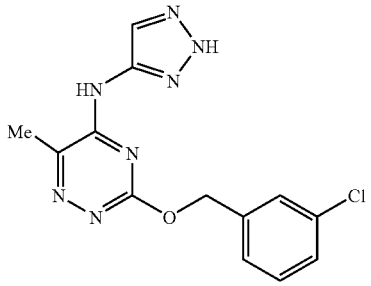

IVa

IVb or a pharmaceutically acceptable salt thereof, wherein $R^{y'}$, $R^{2'}$, $R^2$, Q, Ring D, and subcomponents thereof are as defined above for compounds of formula Ia and formula Ib.

Preferred $R^2$, $R^{2'}$ (including embodiments where $R^2$ and $R^{2'}$ are taken together to form a ring), $R^{y}$, Q, and Ring D groups are as described above for compounds of formula Ia and formula Ib.

Representative compounds of formula IVa and formula IVb are shown below in Tables 4a and 4b.

TABLE 4a

Compounds of Formula IVa

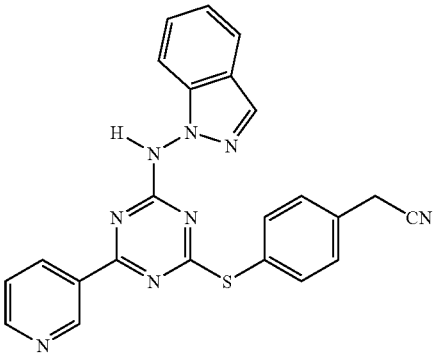

IVa-1

IVa-2

IVa-3

TABLE 4b

Compounds of Formula IVb

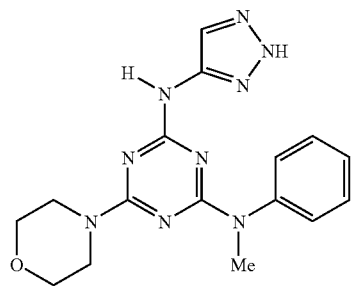

IVb-1

TABLE 4b-continued

Compounds of Formula IVb

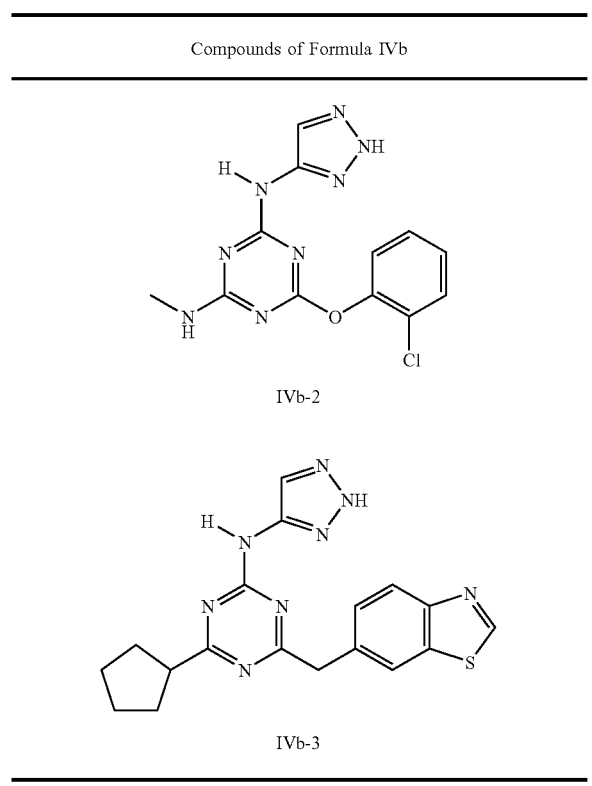

IVb-2

IVb-3

4. General Synthetic Methodology:

The compounds of this invention may be prepared in general by methods known to those skilled in the art for analogous compounds, as illustrated by the general schemes Ia and Ib to Va and Vb below.

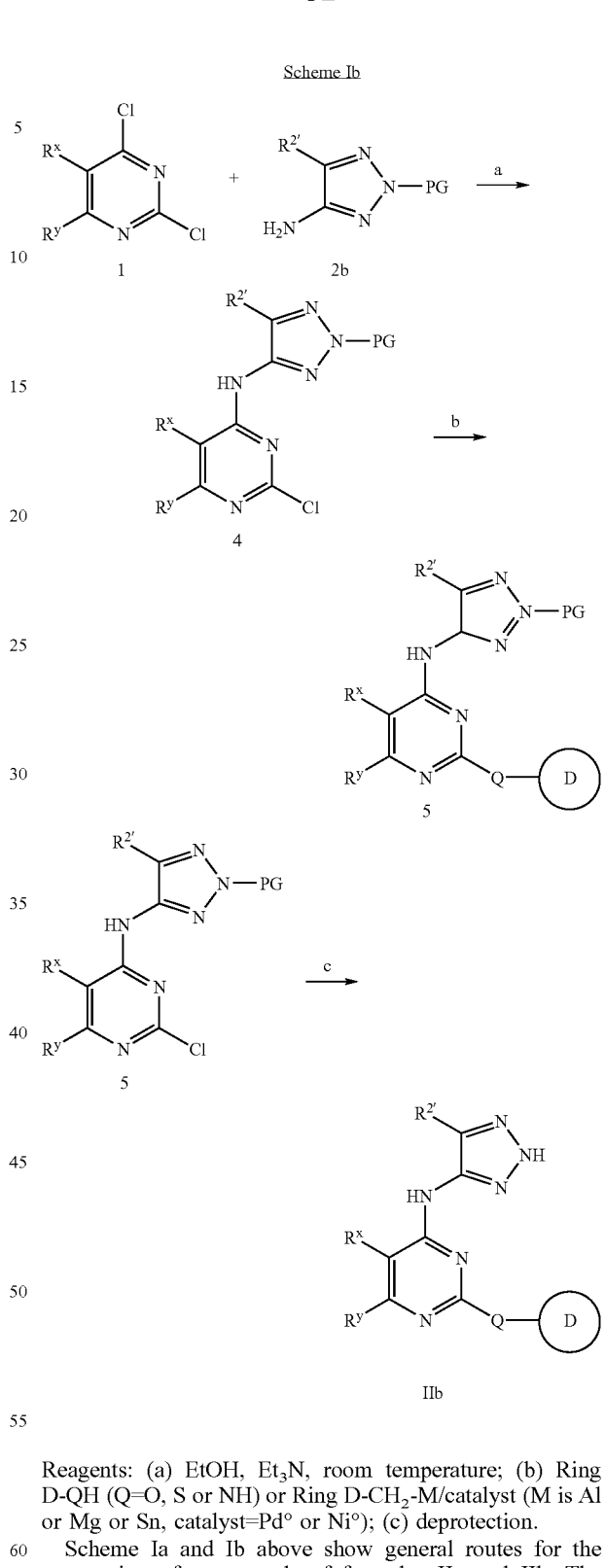

Reagents: (a) EtOH, Et₃N, room temperature; (b) Ring D-QH (Q=O, S or NH) or Ring D-CH₂-M/catalyst (M is Al or Mg or Sn, catalyst=Pd° or Ni°).

Reagents: (a) EtOH, Et₃N, room temperature; (b) Ring D-QH (Q=O, S or NH) or Ring D-CH₂-M/catalyst (M is Al or Mg or Sn, catalyst=Pd° or Ni°); (c) deprotection.

Scheme Ia and Ib above show general routes for the preparation of compounds of formulae IIa and IIb. The dichlorinated starting material 1 may be prepared using methods similar to the those reported in *J. Indian. Chem. Soc.*, 61, 690–693 (1984) or in *J. Med. Chem.*, 37, 3828–3833 (1994). The reaction of 1 with aminoheterocycle 2a or 2b in a manner as described in *Bioorg. Med. Chem. Lett*, 10, 11, 1175–1180, (2000) or in *J. Het. Chem*, 21, 1161–1167, (1984) provides the versatile monochloro intermediates 3 or 4. Conditions for displacing the chloro groups of 3 or 4 by Ring D-QH will depend on the nature of the Q linker moiety and are generally known in the field. See, for example, *J. Med. Chem,* 38, 14, 2763–2773, (1995) (where Q is an N-Link), *Chem. Pharm. Bull.,* 40, 1, 227–229, (1992) (S-Link), or *J. Het. Chem.,* 21, 1161–1167, (1984) (O-Link) or *Bioorg. Med. Chem. Lett,* 8, 20, 2891–2896, (1998) (C-Link). Conditions for removal of protecting group PG from intermediate 5 to provide compounds IIb of the present invention are similar to those found in *Protective Groups in Organic Synthesis* 1991, 2$^{nd}$ edition, John Wiley & Sons, Inc. Publishers, T. W. Greene and P. G. M. Wuts.

Scheme IIa

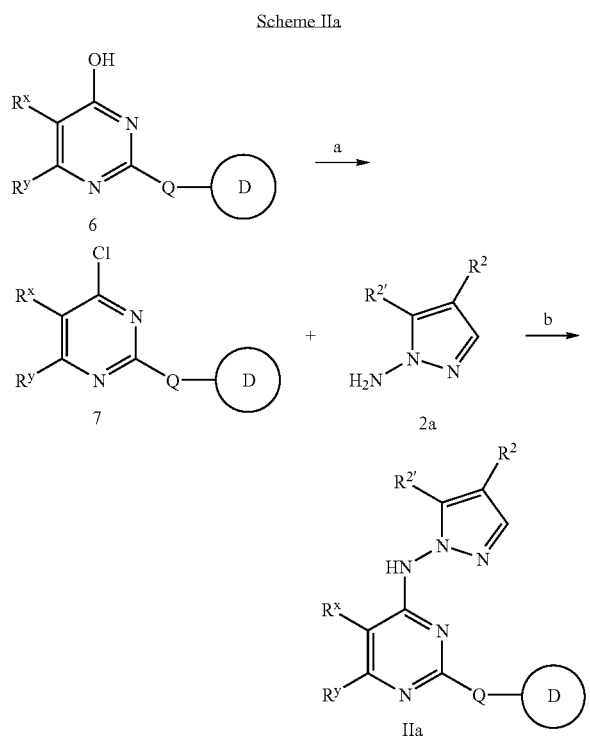

Reagents: (a) POCl$_3$, Pr$_3$N, 110° C.; (b) EtOH, Et$_3$N, room temperature.

Scheme IIb

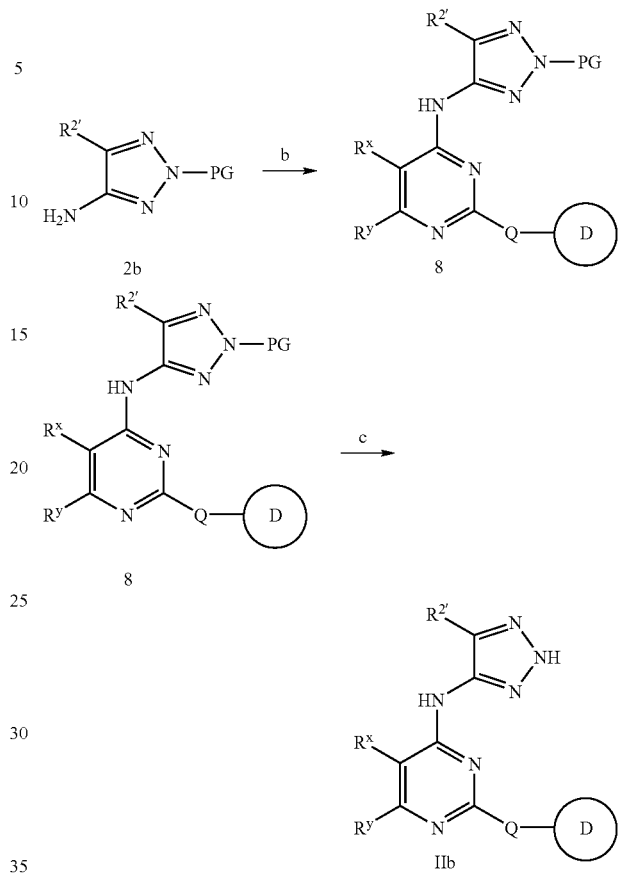

Reagents: (a) POCl$_3$, Pr$_3$N, 110° C.; (b) EtOH, Et$_3$N, room temperature; (c) deprotection.

Scheme IIa and IIb above show alternate routes for the preparation of the present compounds of formulae IIa and IIb. The starting material 6 may be prepared in a manner similar to that described for analogous compounds. See *Chem. Heterocycl. Compd.,* 35, 7, 818–820 (1999) (where Q is an N-Link), *Indian J. Chem. Sect. B,* 22, 1, 37–42 (1983) (N-Link), *Pestic. Sci,* 47, 2, 103–114 (1996) (O-Link), *J. Med. Chem.,* 23, 8, 913–918 (1980) (S-Link), or *Pharmazie,* 43, 7, 475–476 (1988) (C-Link). The chlorination of 6 provides intermediate 7. See *J. Med. Chem.,* 43, 22, 4288–4312 (2000) (Q is an N-Link), *Pestic. Sci,* 47, 2, 103–114 (1996) (O-Link), *J. Med. Chem.,* 41, 20, 3793–3803 (1998) (S-Link), or *J. Med. Chem.,* 43, 22, 4288–4312 (2000) (C-Link). Displacement of the 4-Cl group in intermediate 7 with aminoheterocycle 2a may be performed according to known methods for analogous compounds and provides compounds of formula IIa. See *J. Med. Chem.,* 38, 14, 2763–2773 (1995) (where Q is an N-Link), *Bioorg. Med. Chem. Lett.,* 7, 4, 421–424 (1997) (O-Link), *Bioorg. Med. Chem. Lett.,* 10, 8, 703–706 (2000) (S-Link), or *J. Med. Chem.,* 41, 21, 4021–4035 (1998) (C-Link). Deprotection of intermediate 8 (see *Protective Groups in Organic Synthesis* 1991, 2$^{nd}$ edition, John Wiley & Sons, Inc. Publishers, T. W. Greene and P. G. M. Wuts) provides compound of formula IIb.

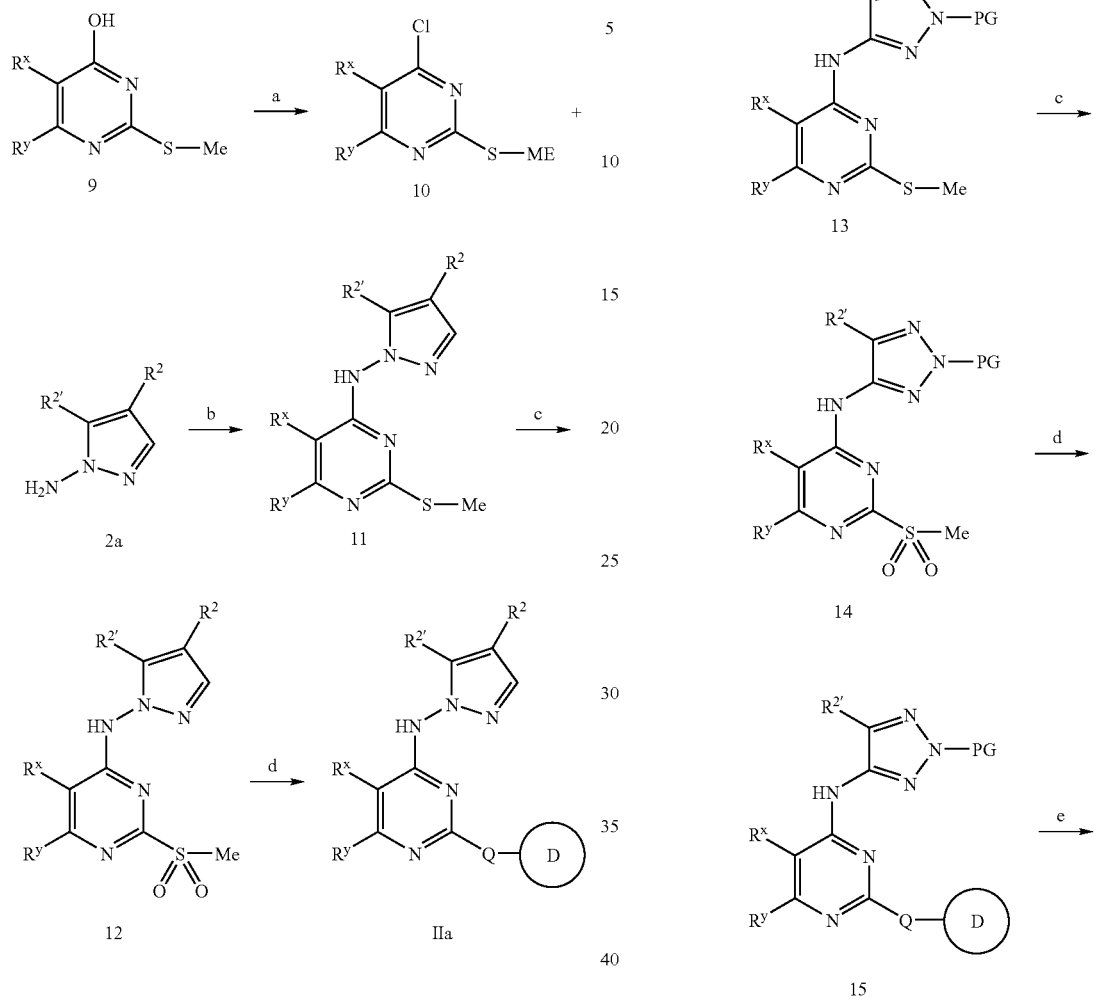

Reagents: (a) POCl₃; (b) EtOH, Et₃N, room temperature; (c) oxone; (d) Ring D-QH (Q=O, S or NH) or Ring D-CH₂-M/ catalyst (M is Al or Mg or Sn, catalyst=Pd° or Ni°).

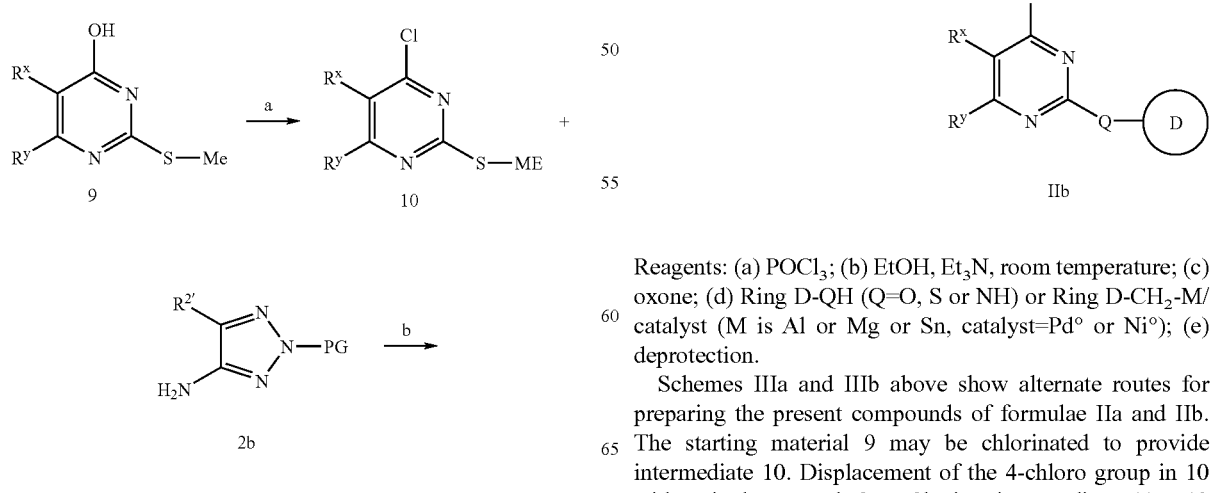

Reagents: (a) POCl₃; (b) EtOH, Et₃N, room temperature; (c) oxone; (d) Ring D-QH (Q=O, S or NH) or Ring D-CH₂-M/ catalyst (M is Al or Mg or Sn, catalyst=Pd° or Ni°); (e) deprotection.

Schemes IIIa and IIIb above show alternate routes for preparing the present compounds of formulae IIa and IIb. The starting material 9 may be chlorinated to provide intermediate 10. Displacement of the 4-chloro group in 10 with aminoheterocycle 2a or 2b gives intermediates 11 or 13 which, upon oxidation of the methylsulfanyl group, provides the methylsulfone 12 or 14. Displacement of the methylsulfonyl group of 12 with Ring D-QH provides compounds of formula IIa. See *J. Am. Chem. Soc.,* 81, 5997–6006 (1959) (where Q is an N-Link) or in *Bioorg. Med. Chem. Lett.,* 10, 8, 821–826 (2000) (S-Link). Displacement of the methylsulfonyl group of 14 with Ring D-QH provides intermediate 15. Deprotection of intermediate 15 (see *Protective Groups in Organic Synthesis* 1991, 2$^{nd}$ edition, John Wiley & Sons, Inc. Publishers, T. W. Greene and P. G. M. Wuts) provides compounds of formula IIb.

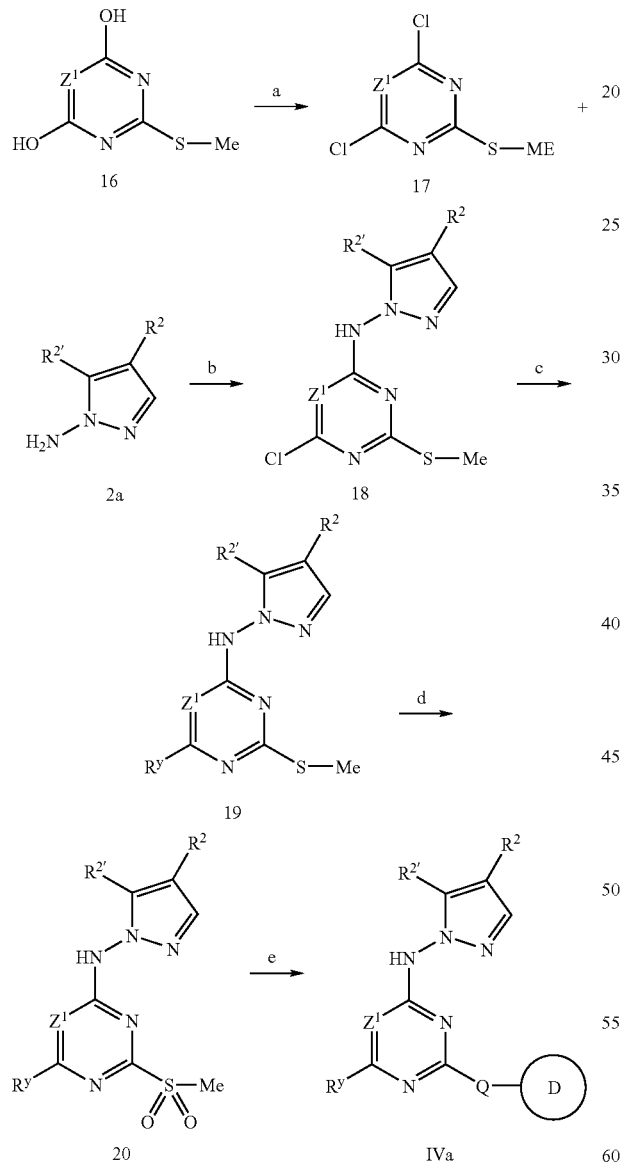

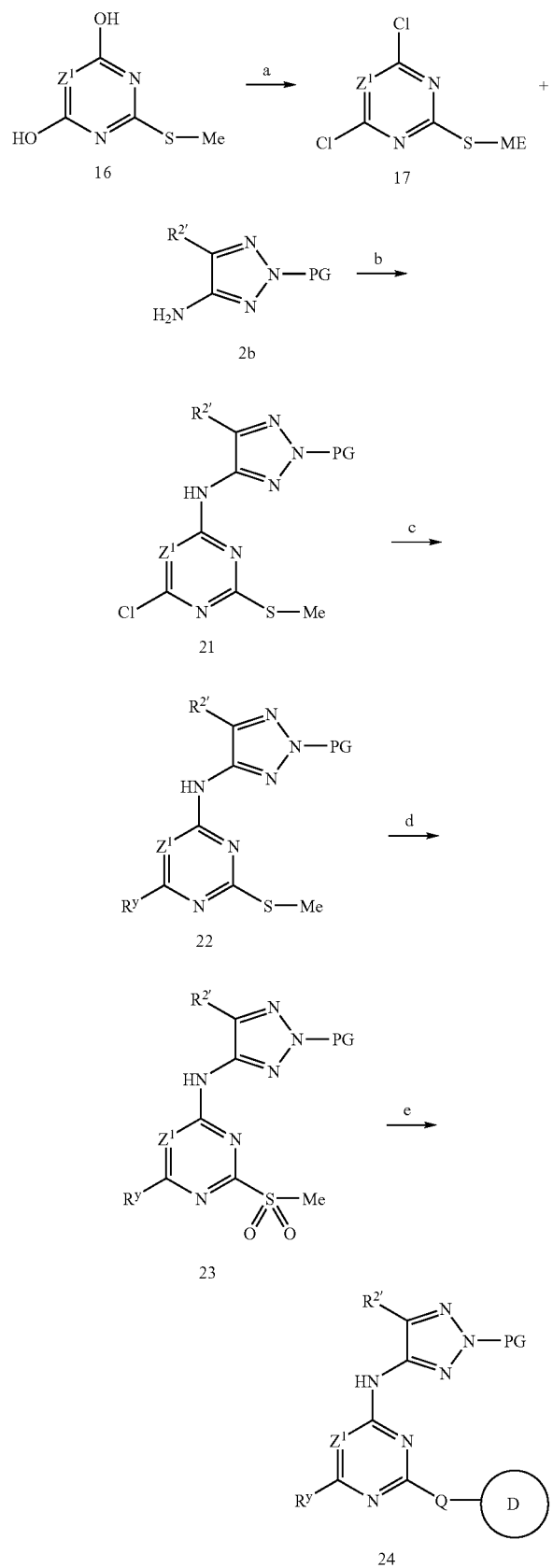

Reagents: (a) POCl$_3$; (b) EtOH, Et$_3$N, room temperature; (c) R$^y$—H (R=S, NH or O); (d) oxone; (e) Ring D-QH (Q=O, S or NH) or R$^1$—CH$_2$-M/catalyst (M is Al or Mg or Sn, catalyst=Pd° or Ni°).

-continued

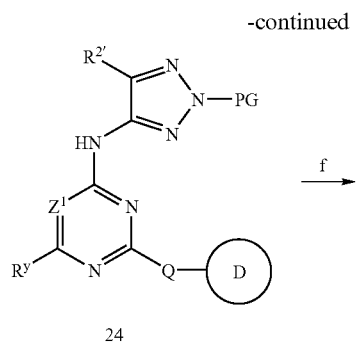

24

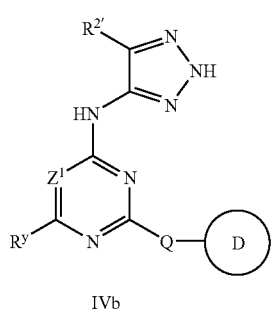

IVb

Reagents: (a) POCl$_3$; (b) EtOH, Et$_3$N, room temperature; (c) R$^y$—H (R=S, NH or O); (d) oxone; (e) Ring D-QH (Q=O, S or NH) or R$^1$—CH$_2$-M/catalyst (M is Al or Mg or Sn, catalyst=Pd° or Ni°); (f) deprotection.

Schemes IVa and IVb above show general routes for the preparation of the compounds of formula IIa and formula IIb, formula IIIa and formula IIIb, or formula IVa and formula IVb wherein R$^y$ is a group attached to the pyrimidine core via a nitrogen, oxygen, or sulfur heteroatom. The starting 4,6-dihydroxy-2-methylsulfanylpyrimidine 16 may be prepared as described in *J. Med. Chem.*, 27, 12, 1621–1629 (1984). The chloro groups of intermediate 17 may be displaced sequentially with aminoheterocycle 2a or 2b and then with another amine (or alcohol or thiol) following procedures similar to those reported in U.S. Pat. No. 2,585,906 (ICI, 1949). The methylsulfanyl group of 19 or 22 may then be oxidized to provide the methylsulfones 20 or 23. Displacement of the methylsulfonyl group of 20 provides compounds of formula IVa. Displacement of the methylsulfonyl group of 23 followed by deprotection of intermediate 24 (see *Protective Groups in Organic Synthesis* 1991, 2$^{nd}$ edition, John Wiley & Sons, Inc. Publishers, T. W. Greene and P. G. M. Wuts) provides compounds of formula IVb.

Scheme Va

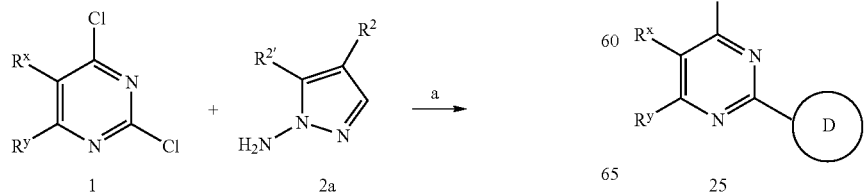

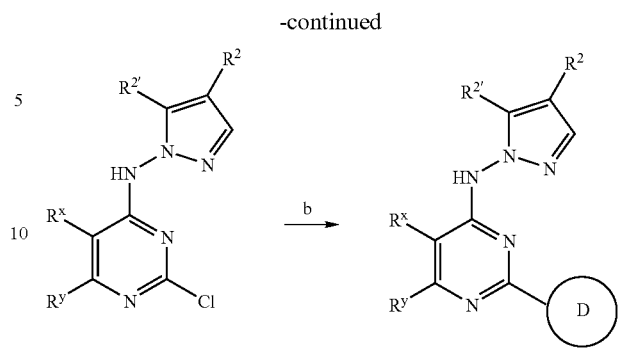

Reagents: (a) EtOH, Et$_3$N, room temperature; (b) Ring D-B(OH)$_2$, PdCl$_2$(dppf), P(t-Bu)$_3$, 2M Na$_2$CO$_3$, DMF, 80° C.

Scheme Vb

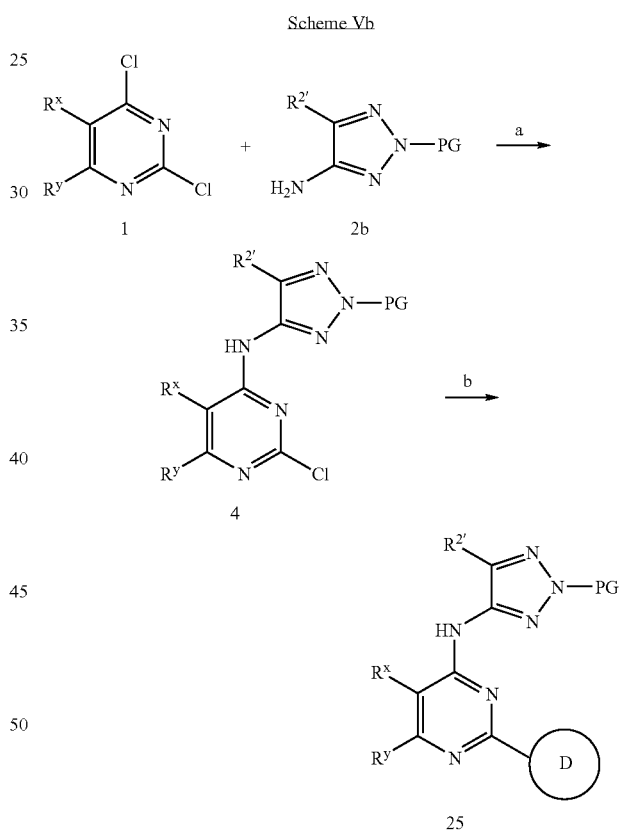

-continued

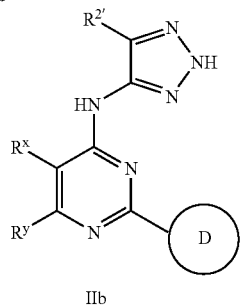

IIb

Reagents: (a) EtOH, Et₃N, room temperature; (b) Ring D-B(OH)₂, PdCl₂(dppf), P(t-Bu)₃, 2M Na₂CO₃, DMF, 80° C; (c) deprotection.

Schemes Va and Vb are general routes for the preparation of compounds of formula II, formula III, or formula IV wherein Q is a valence bond. Preparation of the starting dichloropyrimidine 1 may be achieved in a manner similar to that described in *Chem. Pharm. Bull.*, 30, 9, 1982, 3121–3124. The chlorine in position 4 of intermediate 1 may be replaced by aminoheterocycle 2a or 2b to provide intermediates 3 or 4 in a manner similar to that described in *J. Med. Chem.*, 38, 3547–3557 (1995). Ring D may be introduced on intermediate 3 using a boronic acid under palladium catalysis (see *Tetrahedron*, 48, 37, 1992, 8117–8126) to provide compounds of formula IIa, formula IIIa, or formula IVa. Ring D is similarly introduced for intermediate 4 followed by deprotection of intermediate 25 (see *Protective Groups in Organic Synthesis* 1991, 2$^{nd}$ edition, John Wiley & Sons, Inc. Publishers, T. W. Greene and P. G. M. Wuts) to provide compounds of formula IIb, formula IIIb or formula IVb.

Although certain exemplary embodiments are depicted and described above and herein, it will be appreciated that a compounds of the invention can be prepared according to the methods described generally above using appropriate starting materials by methods generally available to one of ordinary skill in the art.

5. Uses, Formulation and Administration

Pharmaceutically Acceptable Compositions

As discussed above, the present invention provides compounds that are inhibitors of protein kinases, and thus the present compounds are useful for the treatment of diseases, disorders, and conditions including, but not limited to cancer, a proliferative disorder, a cardiac disorder, a neurodegenerative disorder, an autoimmune disorder, a condition associated with organ transplant, an inflammatory disorder, an immunologically mediated disorder, a viral disease, or a bone disorder. Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of a GSK-3, Aurora-2 or Src kinase.

Pharmaceutically acceptable salts are well known in the art. For example, S. M. Berge et al., describe pharmaceutically acceptable salts in detail in *J. Pharmaceutical Sciences*, 1977, 66, 1–19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N⁺ (C₁₋₄alkyl)₄ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, a method for the treatment or lessening the severity of cancer, a proliferative disorder, a cardiac disorder, a neurodegenerative disorder, an autoimmune disorder, a condition associated with organ transplant, an inflammatory disorder, an immunologically mediated disorder, a viral disease, or a bone disorder is provided comprising administering an effective amount of a compound, or a pharmaceutically acceptable composition comprising a compound to a subject in need thereof. In certain embodiments of the present invention an "effective amount" of the compound or pharmaceutically acceptable composition is that amount effective for the treatment or lessening the severity of cancer, a proliferative disorder, a cardiac disorder, a neurodegenerative disorder, an autoimmune disorder, a condition associated with organ transplant, an inflammatory disorder, an immunologically mediated disorder, a viral disease, or a bone disorder. The compounds and compositions, according to the method of the present invention, may be administered using any amount and any route of administration effective for treating or lessening the severity of cancer, a proliferative disorder, a cardiac disorder, a neurodegenerative disorder, an autoimmune disorder, a condition associated with organ transplant, an inflammatory disorder, an immunologically mediated disorder, a viral disease, or a bone disorder. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, car drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of protein kinases. In one embodiment, the compounds and compositions of the invention are inhibitors of one or more of Aurora-2, GSK-3 or Src kinase, and thus, without wishing to be bound by any particular theory, the compounds and compositions are particularly useful for treating or lessening the severity of a disease, condition, or disorder where activation of one or more of Aurora-2, GSK-3 or Src kinase is implicated in the disease, condition, or disorder. When activation of Aurora-2, GSK-3 or Src is implicated in a particular disease, condition, or disorder, the disease, condition, or disorder may also be referred to as "Aurora-2-, GSK-3-, or Src-mediated disease" or disease symptom. Accordingly, in another aspect, the present invention provides a method for treating or lessening the severity of a disease, condition, or disorder where activation or one or more of Aurora-2, GSK-3 or Src is implicated in the disease state.

The activity of a compound utilized in this invention as an inhibitor of Aurora-2, GSK-3 or Src kinase, may be assayed in vitro, in vivo or in a cell line. In vitro assays include assays that determine inhibition of either the phosphorylation activity or ATPase activity of activated Aurora-2, GSK-3 or Src kinase. Alternate in vitro assays quantitate the ability of the inhibitor to bind to Aurora-2, GSK-3 or Src kinase. Inhibitor binding may be measured by radiolabelling the inhibitor prior to binding, isolating the inhibitor/Aurora-2, GSK-3 or Src kinase, complex and determining the amount of radiolabel bound. Alternatively, inhibitor binding may be determined by running a competition experiment where new inhibitors are incubated with Aurora-2, GSK-3 or Src kinase bound to known radioligands.

The term "measurably inhibit", as used herein means a measurable change in Aurora-2, GSK-3 or Src activity between a sample comprising said composition and a Aurora-2, GSK-3 or Src kinase and an equivalent sample comprising Aurora-2, GSK-3 or Src kinase in the absence of said composition.

The term "Aurora-2-mediated disease" or "Aurora-2-mediated condition", as used herein, means any disease or other deleterious condition in which Aurora is known to play a role. The terms "Aurora-2-mediated disease" or "Aurora-2-mediated condition" also mean those diseases or conditions that are alleviated by treatment with an Aurora-2 inhibitor. Such conditions include, without limitation, colon, breast, stomach, and ovarian cancer. The term "Aurora-2-mediated disease", as used herein, means any disease or other deleterious condition or disease in which Aurora-2 is known to play a role. Such diseases or conditions include, without limitation, cancers such as colon and breast cancer.

The term "GSK-3-mediated disease" as used herein, means any disease or other deleterious condition or disease in which GSK-3 is known to play a role. Such diseases or conditions include, without limitation, autoimmune diseases, inflammatory diseases, metabolic, neurological and neurodegenerative diseases, cardiovascular diseases, allergy, asthma, diabetes, Alzheimer's disease, Huntington's disease, Parkinson's disease, AIDS-associated dementia, amyotrophic lateral sclerosis (AML, Lou Gehrig's disease), multiple sclerosis (MS), schizophrenia, cardiomyocyte hypertrophy, reperfusion/ischemia, stroke, and baldness.

The terms "Src-mediated disease" or "Src-mediated condition", as used herein mean any disease or other deleterious condition in which Src is known to play a role. The terms "Src-mediated disease" or "Src-mediated condition" also mean those diseases or conditions that are alleviated by treatment with a Src inhibitor. Such conditions include, without limitation, hypercalcemia, osteoporosis, osteoarthritis, cancer, symptomatic treatment of bone metastasis, and Paget's disease. Src protein kinase and its implication in various diseases has been described [Soriano, *Cell,* 1992, 69, 551; Soriano et al., *Cell* 1991, 64, 693; Takayanagi, *J. Clin. Invest.* 1999, 104, 137; Boschelli, *Drugs of the Future* 2000, 25 (7), 717; Talamonti, *J. Clin. Invest.* 1993, 91, 53; Lutz, *Biochem. Biophys. Res.* 1998, 243, 503; Rosen, *J. Biol. Chem.,* 1986, 261, 13754; Bolen, *Proc. Natl. Acad. Sci. USA* 1987, 84, 2251; Masaki, *Hepatology* 1998, 27, 1257; Biscardi, *Adv. Cancer Res.* 1999, 76, 61; Lynch, *Leukemia* 1993, 7, 1416; Wiener, *Clin. Cancer Res.* 1999, 5, 2164; Staley, *Cell Growth Diff.,* 1997, 8, 269].

In other embodiments, the invention relates to a method of enhancing glycogen synthesis and/or lowering blood levels of glucose in a patient in need thereof, comprising administering to said patient a therapeutically effective amount of a composition comprising a compound of formula I. This method is especially useful for diabetic patients.

In yet another embodiment, the invention relates to a method of inhibiting the production of hyperphosphorylated Tau protein in a patient in need thereof, comprising administering to said patient a therapeutically effective amount of a composition comprising a compound of formula I. This method is especially useful in halting or slowing the progression of Alzheimer's disease.

In still other embodiments, the invention relates to a method of inhibiting the phosphorylation of β-catenin in a patient in need thereof, comprising administering to said patient a therapeutically effective amount of a composition comprising a compound of formula I. This method is especially useful for treating schizophrenia.

According to another embodiment, the method of the present invention relates to treating or lessening the severity of a disease or condition selected from allergy, asthma, diabetes, Alzheimer's disease, Huntington's disease, Parkinson's disease, AIDS-associated dementia, amyotrophic lateral sclerosis (AML, Lou Gehrig's disease), multiple sclerosis (MS), schizophrenia, cardiomyocyte hypertrophy, reperfusion/ischemia, stroke, rheumatoid arthritis, baldness, or leukemia.

According to a preferred embodiment, the method of the present invention relates to treating or lessening the severity of cancer, diabetes, Alzheimer's disease, osteoporosis, transplant rejection, stroke, rheumatoid arthritis or schizophrenia.

According to a more preferred embodiment, the method of the present invention relates to lessening the severity of colon, stomach, breast, hepatic, pancreatic, or ovarian cancer or certain B-cell leukemias and lymphomas.

More preferably, the present invention relates to a method for treating or lessening the severity of stroke.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

For example, chemotherapeutic agents or other anti-proliferative agents may be combined with the compounds of this invention to treat proliferative diseases and cancer. Examples of known chemotherapeutic agents include, but are not limited to, For example, other therapies or anticancer agents that may be used in combination with the inventive anticancer agents of the present invention include surgery, radiotherapy (in but a few examples, gamma-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), Gleevec™, adriamycin, dexamethasone, and cyclophosphamide. For a more comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

Other examples of agents the inhibitors of this invention may also be combined with include, without limitation: treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating implantable medical devices, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device.

Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids or combinations thereof to impart controlled release characteristics in the composition.

Another aspect of the invention relates to inhibiting Aurora-2, GSK-3, or Src activity in a biological sample or a patient, which method comprises administering to the patient, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of Aurora-2, GSK-3, or Src kinase activity in a biological sample is useful for a variety of purposes that are known to one of skill in the art. Examples of such purposes include, but are not limited to, blood transfusion, organ-transplantation, biological specimen storage, and biological assays.

EXAMPLES

Example 1

Aurora-2 Inhibition Assay

Compounds are screened in the following manner for their ability to inhibit Aurora-2 using a standard coupled enzyme assay (Fox et al., *Protein Sci.* 1998, 7, 2249).

To an assay stock buffer solution containing 0.1M HEPES 7.5, 10 mM $MgCl_2$, 1 mM DTT, 25 mM NaCl, 2.5 mM phosphoenolpyruvate, 300 mM NADH, 30 mg/ml pyruvate kinase, 10 mg/ml lactate dehydrogenase, 40 mM ATP, and 800 µM peptide (American Peptide, Sunnyvale, Calif.) is added a DMSO solution of a compound of the present invention to a final concentration of 30 µM. The resulting mixture is incubated at 30° C. for 10 min. The reaction is initiated by the addition of 10 µl of Aurora-2 stock solution to give a final concentration of 70 nM in the assay. The rates of reaction are obtained by monitoring absorbance at 340 nm over a 5 minute read time at 30° C. using a BioRad Ultramark plate reader (Hercules, Calif.). The $K_i$ values are determined from the rate data as a function of inhibitor concentration.

Example 2

GSK-3 Inhibition Assay

Compounds of the present invention are screened for their ability to inhibit GSK-3β (AA 1-420) activity using a standard coupled enzyme system (Fox et al., *Protein Sci.* 1998, 7, 2249). Reactions are carried out in a solution containing 100 mM HEPES (pH 7.5), 10 MM $MgCl_2$, 25 mM NaCl, 300 µM NADH, 1 mM DTT and 1.5% DMSO. Final substrate concentrations in the assay are 20 µM ATP (Sigma Chemicals, St Louis, Mo.) and 300 µM peptide (American Peptide, Sunnyvale, Calif.). Reactions are carried out at 30° C. and 20 nM GSK-3β. Final concentrations of the components of the coupled enzyme system are 2.5 mM phosphoenolpyruvate, 300 µM NADH, 30 µg/ml pyruvate kinase and 10 µg/ml lactate dehydrogenase.

An assay stock buffer solution is prepared containing all of the reagents listed above with the exception of ATP and the test compound of the present invention. The assay stock buffer solution (175 μl) is incubated in a 96 well plate with 5 μl of the test compound of the present invention at final concentrations spanning 0.002 μM to 30 μM at 30° C. for 10 min. Typically, a 12 point titration is conducted by preparing serial dilutions (from 10 mM compound stocks) with DMSO of the test compounds of the present invention in daughter plates. The reaction is initiated by the addition of 20 μl of ATP (final concentration 20 μM). Rates of reaction are obtained using a Molecular Devices Spectramax plate reader (Sunnyvale, Calif.) over 10 min at 30° C. The $K_i$ values are determined from the rate data as a function of inhibitor concentration.

Example 3

SRC Inhibition Assay

The compounds of the present invention are evaluated as inhibitors of human Src kinase using either a radioactivity-based assay or spectrophotometric assay.

Src Inhibition Assay A: Radioactivity-Based Assay

The compounds of the present invention are assayed as inhibitors of full length recombinant human Src kinase (from Upstate Biotechnology, Cat. No. 14-117) expressed and purified from baculo viral cells. Src kinase activity is monitored by following the incorporation of $^{33}P$ from ATP into the tyrosine of a random poly Glu-Tyr polymer substrate of composition, Glu:Tyr=4:1 (Sigma, Cat. No. P-0275). The final concentrations of the assay components are: 0.05 M HEPES (pH 7.6), 10 mM $MgCl_2$, 2 mM DTT, 0.25 mg/ml BSA, 10 μM ATP (1–2 μCi $^{33}P$-ATP per reaction), 5 mg/ml poly Glu-Tyr, and 1–2 units of recombinant human Src kinase. In a typical assay, all the reaction components with the exception of ATP are pre-mixed and aliquoted into assay plate wells. Compounds of the present invention are dissolved in DMSO and added to the wells to give a final DMSO concentration of 2.5%. The assay plate is incubated at 30° C. for 10 min before initiating the reaction with $^{33}P$-ATP. After 20 min of reaction, the reactions are quenched with 150 μl of 10% trichloroacetic acid (TCA) containing 20 mM $Na_3PO_4$. The quenched samples are then transferred to a 96-well filter plate (Whatman, UNI-Filter GF/F Glass Fiber Filter, Cat No. 7700–3310) installed on a filter plate vacuum manifold. Filter plates are washed four times with 10% TCA containing 20 mM $Na_3PO_4$ and then 4 times with methanol. 200 μl of scintillation fluid is then added to each well. The plates are sealed and the amount of radioactivity associated with the filters is quantified on a TopCount scintillation counter. The radioactivity incorporated is plotted as a function of the compound of the present invention concentration. The data is fitted to a competitive inhibition kinetics model to give the $K_i$ values for the compounds of the present invention.

Src Inhibition Assay B: Spectrophotometric Assay

The ADP produced from ATP by the human recombinant Src kinase-catalyzed phosphorylation of poly Glu-Tyr substrate is quantified using a coupled enzyme assay (Fox et al., *Protein Sci.* 1998, 7, 2249). In this assay one molecule of NADH is oxidised to NAD for every molecule of ADP produced in the kinase reaction. The disappearance of NADH is conveniently followed at 340 nm.

The final concentrations of the assay components are: 0.025 M HEPES (pH 7.6), 10 mM $MgCl_2$, 2 mM DTT, 0.25 mg/ml poly Glu-Tyr, and 25 nM of recombinant human Src kinase. Final concentrations of the components of the coupled enzyme system are 2.5 mM phosphoenolpyruvate, 200 μM NADH, 30 μg/ml pyruvate kinase and 10 μg/ml lactate dehydrogenase.

In a typical assay, all the reaction components with the exception of ATP are pre-mixed and aliquoted into assay plate wells. Compounds of the present invention dissolved in DMSO are added to the wells to give a final DMSO concentration of 2.5%. The assay plate is incubated at 30° C. for 10 min before initiating the reaction with 100 μM ATP. The absorbance change at 340 nm over time is monitored on a molecular devices plate reader. The data is fitted to a competitive inhibition kinetics model to get the $K_i$ values for the compounds of the present invention.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A compound of formula Ia or Ib:

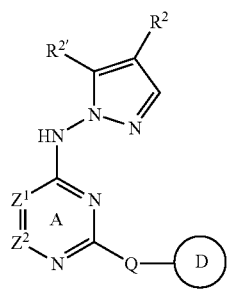

Ia

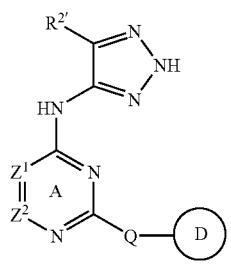

Ib or a pharmaceutically acceptable salt thereof, wherein:

$R^2$ is —R, oxo, halogen, —CN, —$NO_2$, —$CO_2R$, —Ar, -T-Ar, or -T-R;

$R^{2'}$ is R, or $R^2$ and $R^{2'}$ are taken together to form a optionally substituted 5–7 membered, partially unsaturated or fully unsaturated ring having zero to two ring heteroatoms independently selected from nitrogen, oxygen, or sulfur, wherein said optional substituents are selected from:

halogen; —R°; —OR°; —SR°; 1,2-methylene-dioxy; 1,2-ethylenedioxy; phenyl (Ph) optionally substituted with R°; —O(Ph) optionally substituted with R°; —$(CH_2)_{1-2}$(Ph), optionally substituted with R°; —CH═CH(Ph), optionally substituted with R°; —$NO_2$; —CN; —$N(R°)_2$; —NR°C(O)R°; —NR°C(S)R°; —NR°C(O)N$(R°)_2$;

—NR°C(S)N(R°)$_2$; —NR°CO$_2$R°; —NR°NR°C(O)R°; —NR°NR°C(O)N(R°)$_2$; —NR°NR°CO$_2$R°; —C(O)C(O)R°; —C(O)CH$_2$C(O)R°; —CO$_2$R°; —OC(O)R°; —C(O)R°; —C(S)R°; —C(O)N(R°)$_2$; —OC(O)N(R°)$_2$; —C(NOR°)R°; —S(O)R°; —S(O)$_2$R°; —S(O)$_3$R°; —SO$_2$N(R°)$_2$; —NR°SO$_2$N(R°)$_2$; —NR°SO$_2$R°; —N(OR°)R°; —C(=S)N(R°)$_2$; —C(=NH)—N(R°)$_2$; or —(CH$_2$)$_{0-2}$NHC(O)R° wherein each independent occurrence of R° is selected from hydrogen, C$_{1-6}$ aliphatic optionally substituted with NH$_2$, NH(C$_{1-4}$aliphatic), N(C$_{1-4}$aliphatic)$_2$, halogen, C$_{1-4}$aliphatic, OH, O(C$_{1-4}$aliphatic), NO$_2$, CN, CO$_2$H, CO$_2$(C$_{1-4}$aliphatic), O(haloC$_{1-4}$ aliphatic), or haloC$_{1-4}$aliphatic, wherein each of said C$_{1-4}$aliphatic groups of R° is unsubstituted, an unsubstituted 5–6 membered heteroaryl or heterocyclic ring, phenyl, —O(Ph), or —CH$_2$(Ph), or two independent occurrences of R°, on the same substituent or different substituents, taken together with the atom(s) to which each R° group is bound, form a 3–8-membered cycloalkyl, heterocyclyl, aryl, or heteroaryl ring having 0–3 heteroatoms independently selected from nitrogen, oxygen, or sulfur;

each substitutable ring nitrogen of the ring formed by R$^2$ and R$^{2'}$ is optionally substituted with —R$^+$, —N(R$^+$)$_2$, —C(O)R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^+$)$_2$, —C(=NH)—N(R$^+$)$_2$, or —NR$^+$SO$_2$R$^+$; wherein R$^+$ is hydrogen, an optionally substituted C$_{1-6}$ aliphatic, phenyl, —O(Ph), —CH$_2$(Ph), —(CH$_2$)$_{1-2}$(Ph), —CH=CH(Ph), wherein said optional substituents on said C$_{1-6}$ aliphatic, phenyl, —O(Ph), —CH$_2$(Ph), —(CH$_2$)$_{1-2}$(Ph), —CH=CH(Ph) are selected from NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo(C$_{1-4}$ aliphatic), wherein each of said C$_{1-4}$aliphatic groups of R$^+$ is unsubstituted;

or an unsubstituted 5–6 membered heteroaryl or heterocyclic ring having one to four heteroatoms independently selected from oxygen, nitrogen, or sulfur, or, notwithstanding the definition above, two independent occurrences of R$^+$, on the same substituent or different substituents, taken together with the atom(s) to which each R$^+$ group is bound, form a 3–8-members cycloalkyl, heterocyclyl, aryl, or heteroaryl ring having 0–3 heteroatoms independently selected from nitrogen, oxygen, or sulfur;

each occurrence of R is independently hydrogen, Ar, or a C$_{1-6}$ aliphatic group optionally substituted with =O, =S, =NNHR*, =NN(R*)$_2$, =NNHC(O)R*, =NNHCO$_2$(alkyl), =NNHSO$_2$(alkyl), or =NR* wherein each R* is independently selected from hydrogen or an optionally substituted C$_{1-6}$ aliphatic wherein said optional substituents on the aliphatic group of R* are selected from NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo(C$_{1-4}$ aliphatic), wherein each of said C$_{1-4}$aliphatic groups of R* is unsubstituted; halogen; —R°; —OR°; —SR°; 1,2-methylene-dioxy; 1,2-ethylenedioxy; phenyl (Ph) optionally substituted with R°; —O(Ph) optionally substituted with R°; —(CH$_2$)$_{1-2}$(Ph), optionally substituted with R°; —CH=CH(Ph), optionally substituted with R°; —NO$_2$; —CN; —N(R°)$_2$; —NR°C(O)R°; —NR°C(S)R°; —NR°C(O)N(R°)$_2$; —NR°C(S)N(R°)$_2$; —NR°CO$_2$R°; —NR°NR°C(O)R°; —NR°NR°C(O)N(R°)$_2$; —NR°NR°CO$_2$R°; —C(O)C(O)R°; —C(O)CH$_2$C(O)R°; —CO$_2$R°; —OC(O)R°; —C(O)R°; —C(S)R°; —C(O)N(R°)$_2$; —OC(O)N(R°)$_2$; —C(NOR°)R°; —S(O)R°; —S(O)$_2$R°; —S(O)$_3$R°; —SO$_2$N(R°)$_2$; —NR°SO$_2$N(R°)$_2$; —NR°SO$_2$R°; —N(OR°)R°; —C(=S)N(R°)$_2$; —C(=NH)—N(R°)$_2$; or —(CH$_2$)$_{0-2}$NHC(O)R° wherein each independent occurrence of R° is selected from hydrogen, C$_{1-6}$ aliphatic optionally substituted with NH$_2$, NH(C$_{1-4}$aliphatic), N(C$_{1-4}$aliphatic)$_2$, halogen, C$_{1-4}$aliphatic, OH, O(C$_{1-4}$aliphatic), NO$_2$, CN, CO$_2$H, CO$_2$(C$_{1-4}$aliphatic), O(haloC$_{1-4}$ aliphatic), or haloC$_{1-4}$aliphatic, wherein each of said C$_{1-4}$aliphatic groups of R° is unsubstituted, an unsubstituted 5–6 membered heteroaryl or heterocyclic ring, phenyl, —O(Ph), or —CH$_2$(Ph), or two independent occurrences of R°, on the same substituent or different substituents, taken together with the atom(s) to which each R° group is bound, form a 3–8-membered cycloalkyl, heterocyclyl, aryl, or heteroaryl ring having 0–3 heteroatoms independently selected from nitrogen, oxygen, or sulfur;

Z$^1$ is CR$^x$;

R$^x$ is —R, halogen, —N(R)$_2$, —NO$_2$, —CN, —CO$_2$R, —OR, or —SR; wherein two R bound to the same nitrogen atom may be taken together with that nitrogen atom to form a five or six membered heterocyclic or heteroaryl ring having one to two additional heteratoms independently selected from oxygen, nitrogen, or sulfur;

Z$^2$ is CR$^y$;

R$^y$ is —R$^1$, —CN, halogen, —NO$_2$, —Ar, -T-Ar, or -T-R;

R$^1$ is a C$_{1-6}$ aliphatic group optionally substituted with =O, =S, =NNHR*, =NN(R*)$_2$, =NNHC(O)R*, =NNHCO$_2$(alkyl), =NNHSO$_2$(alkyl), or =NR* wherein each R* is independently selected from hydrogen or an optionally substituted C$_{1-6}$ aliphatic wherein said optional substituents on the C$_{1-6}$ aliphatic group of R* are selected from NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo(C$_{1-4}$ aliphatic), wherein each of said C$_{1-4}$ aliphatic groups of R* is unsubstituted; halogen; —R°; —OR°; —SR°; 1,2-methylene-dioxy; 1,2-ethylenedioxy; phenyl (Ph) optionally substituted with R°; —O(Ph) optionally substituted with R°; —(CH$_2$)$_{1-2}$(Ph), optionally substituted with R°; —CH=CH(Ph), optionally substituted with R°; —NO$_2$; —CN; —N(R°)$_2$; —NR°C(O)R°; —NR°C(S)R°; —NR°C(O)N(R°)$_2$; —NR°C(S)N(R°)$_2$; —NR°CO$_2$R°; —NR°NR°C(O)R°; —NR°NR°C(O)N(R°)$_2$; —NR°NR°CO$_2$R°; —C(O)C(O)R°; —C(O)CH$_2$C(O)R°; —CO$_2$R°; —OC(O)R°; —C(O)R°; —C(S)R°; —C(O)N(R°)$_2$; —OC(O)N(R°)$_2$; —C(NOR°)R°; —S(O)R°; —S(O)$_2$R°; —S(O)$_3$R°; —SO$_2$N(R°)$_2$; —NR°SO$_2$N(R°)$_2$; —NR°SO$_2$R°; —N(OR°)R°; —C(=S)N(R°)$_2$; —C(=NH)—N(R°)$_2$; or —(CH$_2$)$_{0-2}$NHC(O)R° wherein each independent occurrence of R° is selected from hydrogen, C$_{1-6}$ aliphatic optionally substituted with NH$_2$, NH(C$_{1-4}$aliphatic), N(C$_{1-4}$aliphatic)$_2$, halogen, C$_{1-4}$aliphatic, OH, O(C$_{1-4}$aliphatic), NO$_2$, CN, CO$_2$H, CO$_2$(C$_{1-4}$aliphatic), O(haloC$_{1-4}$ aliphatic), or haloC$_{1-4}$aliphatic, wherein each of said C$_{1-4}$aliphatic groups of R° is unsubstituted, an unsubstituted 5–6 membered heteroaryl or heterocyclic ring, phenyl, —O(Ph), or —CH$_2$(Ph), or two independent occurrences of R°, on the same substituent or different substituents, taken together with the atom(s) to which each R° group is bound, form a 3–8-membered cycloalkyl, heterocyclyl, aryl, or heteroaryl ring having 0–3 heteroatoms independently selected from nitrogen, oxygen, or sulfur;

each Ar is independently an optionally substituted 3–6 membered heterocyclic ring having one or two heteroatoms independently selected from nitrogen, oxygen, or sulfur; or a 5 or 6 membered aryl ring having zero to three heteroatoms independently selected from nitrogen, oxygen, or sulfur, wherein:

said optional substituents on said Ar are selected from halogen; —R°; —OR°; —SR°; 1,2-methylene-dioxy; 1,2-ethylenedioxy; phenyl (Ph) optionally substituted with R°; —O(Ph) optionally substituted with R°; —(CH$_2$)$_{1-2}$(Ph), optionally substituted with R°; —CH═CH(Ph), optionally substituted with R°; —NO$_2$; —CN; —N(R°)$_2$; —NR°C(O)R°; —NR°C(S)R°; —NR°C(O)N(R°)$_2$; —NR°C(S)N(R°)$_2$; —NR°CO$_2$R°; —NR°NR°C(O)R°; —NR°NR°C(O)N(R°)$_2$; —NR°NR°CO$_2$R°; —C(O)C(O)R°; —C(O)CH$_2$C(O)R°; —CO$_2$R°; —OC(O)R°; —C(O)R°; —C(S)R°; —C(O)N(R°)$_2$; —OC(O)N(R°)$_2$; —C(NOR°)R°; —S(O)R°; —S(O)$_2$R°; —S(O)$_3$R°; —SO$_2$N(R°)$_2$; —NR°SO$_2$N(R°)$_2$; —NR°SO$_2$R°; —N(OR°)R°; —C(═S)N(R°)$_2$; —C(═NH)—N(R°)$_2$; or —(CH$_2$)$_{0-2}$NHC(O)R° wherein each independent occurrence of R° is selected from hydrogen, C$_{1-6}$ aliphatic optionally substituted with NH$_2$, NH(C$_{1-4}$aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(haloC$_{1-4}$ aliphatic), or haloC$_{1-4}$ aliphatic, wherein each of said C$_{1-4}$ aliphatic groups of R° is unsubstituted, an unsubstituted 5–6 membered heteroaryl or heterocyclic ring, phenyl, —O(Ph), or —CH$_2$(Ph), or two independent occurrences of R°, on the same substituent or different substituents, taken together with the atom(s) to which each R° group is bound, form a 3–8-membered cycloalkyl, heterocyclyl, aryl, or heteroaryl ring having 0–3 heteroatoms independently selected from nitrogen, oxygen, or sulfur;

Ar is optionally fused to a five or six membered partially unsaturated, or fully unsaturated ring having zero to two heteroatoms independently selected from nitrogen, oxygen, or sulfur;

T is a C$_{1-4}$ alkylidene chain wherein one methylene unit of T is optionally replaced by —O—, —S—, —C(O)—, —CO$_2$—, —NR—, —NRC(O)—, —NRC(O)NR—, —C(O)C(O)—, —OC(O)NR—, —NRCO$_2$—, —SO$_2$NR—, —NRSO$_2$—, or —NRSO$_2$NR—;

Q is —N(R')—, —S—, —O—, —C(R')$_2$—, or a valence bond, provided that Q is other than a valence bond in compounds of formula Ib; wherein each R' is independently hydrogen or C$_{1-6}$ aliphatic; and Ring D is a 5 or 6 membered optionally substituted monocyclic aryl ring having zero to two heteroatoms independently selected from nitrogen, oxygen, or sulfur; or an eight to ten membered partially unsaturated or fully unsaturated bicyclic ring having zero to four heteroatoms independently selected from nitrogen, oxygen, or sulfur, wherein;

said optional substituents are selected from halogen; —R°; —OR°; —SR°; 1,2-methylene-dioxy; 1,2-ethylenedioxy; phenyl (Ph) optionally substituted with R°; —O(Ph) optionally substituted with R°; —(CH$_2$)$_{1-2}$(Ph), optionally substituted with R°; —CH═CH(Ph), optionally substituted with R°; —NO$_2$; —CN; —N(R°)$_2$; —NR°C(O)R°; —NR°C(S)R°; —NR°C(O)N(R°)$_2$; —NR°C(S)N(R°)$_2$; —NR°CO$_2$R°; —NR°NR°C(O)R°; —NR°NR°C(O)N(R°)$_2$; —NR°NR°CO$_2$R°; —C(O)C(O)R°; —C(O)CH$_2$C(O)R°; —CO$_2$R°; —OC(O)R°; —C(O)R°; —C(S)R°; —C(O)N(R°)$_2$; —OC(O)N(R°)$_2$; —C(NOR°)R°; —S(O)R°; —S(O)$_2$R°; —S(O)$_3$R°; —SO$_2$N(R°)$_2$; —NR°SO$_2$N(R°)$_2$; —NR°SO$_2$R°; —N(OR°)R°; —C(═S)N(R°)$_2$; —C(═NH)—N(R°)$_2$; or —(CH$_2$)$_{0-2}$NHC(O)R° wherein each independent occurrence of R° is selected from hydrogen, C$_{1-6}$ aliphatic optionally substituted with NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(haloC$_{1-4}$ aliphatic), or halo C$_{1-4}$aliphatic, wherein each of said C$_{1-4}$ aliphatic groups of R° is unsubstituted, an unsubstituted 5–6 membered heteroaryl or heterocyclic ring, phenyl, —O(Ph), or —CH$_2$(Ph), or two independent occurrences of R°, on the same substituent or different substituents, taken together with the atom(s) to which each R° group is bound, form a 3–8-membered cycloalkyl, heterocyclyl, aryl, or heteroaryl ring having 0–3 heteroatoms independently selected from nitrogen, oxygen, or sulfur.

2. The compound according to claim 1, wherein:

$R^2$ is —R, halogen, —CN, —NO$_2$, —Ar, -T-Ar, or -T-R;

$R^{2'}$ is —R, or $R^2$ and $R^{2'}$ are taken together to form a five to seven membered, partially unsaturated or fully unsaturated ring having zero to two ring heteroatoms independently selected from nitrogen, oxygen, or sulfur, wherein;

each substitutable ring nitrogen of the ring formed by $R^2$ and $R^{2'}$ is optionally and independently substituted by —R, —C(O)R, —CO$_2$R, —SO$_2$R, —C(O)N(R)$_2$ or —SO$_2$N(R)$_2$, and one to three substitutable ring carbons of the ring formed by $R^2$ and $R^{2'}$ are optionally and independently substituted with —R, —OR, —N(R)$_2$, —SR, —NO$_2$, —CN or halogen;

each occurrence of R is independently hydrogen, C$_{1-6}$ aliphatic, or Ar; wherein R is optionally substituted with one to three groups independently selected from oxo, —CO$_2$R', —Ar, —OR', —N(R')$_2$, —SR', —NO$_2$, halogen, or —CN; wherein each R' is independently hydrogen or C$_{1-6}$ aliphatic, or two R' bound to the same nitrogen atom may be taken together with that nitrogen atom to form a five or six membered heterocyclic or heteroaryl ring having one to two additional heteroatoms independently selected from oxygen, nitrogen, or sulfur;

$Z^1$ is $CR^x$;

$R^x$ is —R, halogen, —N(R)$_2$, —NO$_2$, —CN, —CO$_2$R, —OR, or —SR; wherein two R bound to the same nitrogen atom may be taken together with that nitrogen atom to form a five or six membered heterocyclic or heteroaryl ring having one to two additional heteroatoms independently selected from oxygen, nitrogen, or sulfur;

$Z^2$ is $CR^y$;

$R^y$ is —$R^1$, —CN, halogen, —$NO_2$, —Ar, -T-Ar, or -T-R-;

$R^1$ is hydrogen or a $C_{1-6}$ aliphatic optionally substituted with one to three groups independently selected from oxo, —$CO_2R'$, phenyl, —OR', —$N(R')_2$, —SR', —$NO_2$, halogen, or —CN;

each Ar is independently a three to six membered heterocyclic ring having one or two heteroatoms independently selected from nitrogen, oxygen, or sulfur; or a five or six membered aryl ring having zero to three heteroatoms independently selected from nitrogen, oxygen, or sulfur, wherein:

Ar is optionally fused to a five or six membered partially unsaturated, or fully unsaturated ring having zero to two heteroatoms independently selected from nitrogen, oxygen, or sulfur, and wherein:

Ar is optionally substituted with one to three groups independently selected from —R, —OR, —SR, —CN, —$NO_2$, oxo, halogen, —$N(R)_2$, —C(O)R, —OC(O)R, —$CO_2R$, —$SO_2R$, —$SO_2N(R)_2$, —$N(R)SO_2R$, —C(O)N(R), —$C(O)N(R)_2$, —OC(O)N(R), —$OC(O)N(R)_2$, —N(R)C(O)R, —N(R)C(O)N(R)_2, or —$N(R)CO_2(R)$; and T is a $C_{1-4}$ alkylidene chain wherein one methylene unit of T is optionally replaced by —O—, —S—, —C(O)—, —$CO_2$—, —NR—, —NRC(O)—, —NRC(O)NR—, —C(O)C(O)—, —OC(O)NR—, —$NRCO_2$—, —$SO_2NR$—, —$NRSO_2$—, or —$NRSO_2NR$—;

Q is —N(R')—, —S—, —O—, —$C(R')_2$—, or a valence bond; and

Ring D is a five or six membered monocyclic aryl ring having zero to two heteroatoms independently selected from nitrogen, oxygen, or sulfur; or an eight to ten membered partially unsaturated or fully unsaturated bicyclic ring having zero to four heteroatoms independently selected from nitrogen, oxygen, or sulfur, wherein:

Ring D is optionally substituted with one to three substituents independently selected from —R, -T-R, -T-Ar, halogen, —CN, —$NO_2$, or —Ar.

3. The compound according to claim 1, wherein:

$Z^1$ is $CR^x$;

$Z^2$ is $CR^y$;

$R^x$ is —R, halogen, —$N(R)_2$, —$NO_2$, —CN, —$CO_2R$, —OR, or —SR;

$R^y$ is —$R^1$, —Ar, -T-R, or -T-Ar; and

T is —O—, —NR—, or —S—.

4. The compound according to claim 3, wherein:

$R^x$ is hydrogen, —$N(R)_2$, —OR, or a $C_{1-4}$ aliphatic group;

$R^y$ is $C_{1-4}$ aliphatic, —Ar, -T-$C_{1-4}$ aliphatic, or -T-Ar;

R is hydrogen or $C_{1-4}$ aliphatic;

Ar is a five or six membered heteroaryl or heterocyclic ring having one to two heteroatoms independently selected from nitrogen, oxygen, or sulfur, or phenyl optionally substituted with halogen; —R°; —OR°; —SR°; 1,2-methylene-dioxy; 1,2-ethylenedioxy; phenyl (Ph) optionally substituted with R°; —O(Ph) optionally substituted with R°; —$(CH_2)_{1-2}$(Ph), optionally substituted with R°; —CH=CH(Ph), optionally substituted with R°; —$NO_2$; —CN; —$N(R°)_2$; —NR°C(O)R°; —NR°C(S)R°; —NR°C(O)N(R°)_2; —NR°C(S)N(R°)_2; —$NR°CO_2R°$; —NR°NR°C(O)R°; —NR°NR°C(O)N(R°)_2; —$NR°NR°CO_2R°$; —C(O)C(O)R°; —$C(O)CH_2C(O)R°$; —$CO_2R°$; —OC(O)R°; —C(O)R°; —C(S)R°; —$C(O)N(R°)_2$; —$OC(O)N(R°)_2$; —C(NOR°)R°; —S(O)R°; —$S(O)_2R°$; —$S(O)_3R°$; —$SO_2N(R°)_2$; —$NR°SO_2N(R°)_2$; —$NR°SO_2R°$; —N(OR°)R°; —$C(=S)N(R°)_2$; —C(=NH)—$N(R°)_2$; or —$(CH_2)_{0-2}NHC(O)R°$ wherein each independent occurrence of R° is selected from hydrogen, $C_{1-6}$ aliphatic optionally substituted with $NH_2$, $NH(C_{1-4}aliphatic)$, $N(C_{1-4}$ aliphatic$)_2$, halogen, $C_{1-4}$ aliphatic, OH, $O(C_{1-4}$ aliphatic), $NO_2$, CN, $CO_2H$, $CO_2(C_{1-4}$ aliphatic), $O(haloC_{1-4}$ aliphatic), or $haloC_{1-4}$ aliphatic, wherein each of said $C_{1-4}$ aliphatic groups of R° is unsubstituted, an unsubstituted 5–6 membered heteroaryl or heterocyclic ring, phenyl, —O(Ph), or —$CH_2$(Ph), or two independent occurrences of R°, on the same substituent or different substituents, taken together with the atom(s) to which each R° group is bound, form a 3–8-membered cycloalkyl, heterocyclyl, aryl, or heteroaryl ring having 0–3 heteroatoms independently selected from nitrogen, oxygen, or sulfur; and Q is —N(R')—, —S—, or a valence bond.

5. The compound according to claim 4, wherein:

$R^x$ is hydrogen, methyl, ethyl, cyclopropyl, or isopropyl; and $R^y$ is 2-pyridyl, 3-pyridyl, 4-pyridyl, pyrrolidinyl, imidazolyl, furanyl, thiazolyl, thienyl, piperidinyl, morpholinyl, thiomorpholinyl, piperazinyl, methyl, ethyl, cyclopropyl, isopropyl, t-butyl, methoxyethylamino, methoxymethyl, methoxyethyl, ethylamino, dimethylamino, methylamino, dimethylaminopropyloxy, or acetamido.

6. The compound according to claim 5, wherein:

Ring D is a five or six membered monocyclic aryl ring having zero to two nitrogens; or nine or ten membered partially unsaturated or fully unsaturated bicyclic ring having zero to three heteroatoms independently selected from nitrogen, oxygen, or sulfur, wherein said aryl or bicyclic ring is optionally substituted with halogen; —R°; —OR°; —SR°; 1,2-methylene-dioxy; 1,2-ethylenedioxy; phenyl (Ph) optionally substituted with R°; —O(Ph) optionally substituted with R°; —$(CH_2)_{1-2}$(Ph), optionally substituted with R°; —CH=CH(Ph), optionally substituted with R°; —$NO_2$; —CN; —$N(R°)_2$; —NR°C(O)R°; —NR°C(S)R°; —NR°C(O)N(R°)_2; —NR°C(S)N(R°)_2; —$NR°CO_2R°$; —NR°NR°C(O)R°; —NR°NR°C(O)N(R°)_2; —$NR°NR°CO_2R°$; —C(O)C(O)R°; —$C(O)CH_2C(O)R°$; —$CO_2R°$; —OC(O)R°; —C(O)R°; —C(S)R°; —$C(O)N(R°)_2$; —$OC(O)N(R°)_2$; —C(NOR°)R°; —S(O)R°; —$S(O)_2R°$; —$S(O)_3R°$; —$SO_2N(R°)_2$; —$NR°SO_2N(R°)_2$; —$NR°SO_2R°$; —N(OR°)R°; —$C(=S)N(R°)_2$; —C(=NH)—$N(R°)_2$; or —$(CH_2)_{0-2}NHC(O)R°$ wherein each independent occurrence of R° is selected from hydrogen, $C_{1-6}$ aliphatic optionally substituted with $NH_2$, $NH(C_{1-4}$ aliphatic), $N(C_{1-4}$ aliphatic$)_2$, halogen, $C_{1-4}$ aliphatic, OH, $O(C_{1-4}$ aliphatic), $NO_2$, CN, $CO_2H$, $CO_2(C_{1-4}$ aliphatic), $O(haloC_{1-4}$ aliphatic), or $haloC_{1-4}$ aliphatic, wherein each of said $C_{1-4}$ aliphatic groups of R° is unsubstituted, an unsubstituted 5–6 membered heteroaryl or heterocyclic ring, phenyl, —O(Ph), or —$CH_2$(Ph), or two independent occurrences of R°, on the same substituent or different substituents, taken together with the atom(s) to which each R° group is bound, form a 3–8-membered cycloalkyl, heterocyclyl, aryl, or heteroaryl ring having 0–3 heteroatoms independently selected from nitrogen, oxygen, or sulfur.

7. The compound according to claim 6, wherein:

Ring D is phenyl, imidazolyl, pyrazolyl, pyridyl, pyridazinyl, pyrazinyl, naphthyl, tetrahydronaphthyl, benzimidazolyl, benzthiazolyl, quinolinyl, quinazolinyl, benzodioxinyl, isobenzofuran, indanyl, indolyl, indolinyl, indazolyl, or isoquinolinyl, wherein said Ring D is optionally substituted with halogen; —R°; —OR°; —SR°; 1,2-methylene-dioxy; 1,2-ethylene-dioxy; phenyl (Ph) optionally substituted with R°; —O(Ph) optionally substituted with R°; —(CH$_2$)$_{1-2}$ (Ph), optionally substituted with R°; —CH=CH(Ph), optionally substituted with R°; —NO$_2$; —CN; —N(R°)$_2$; —NR°C(O)R°; —NR°C(S)R°; —NR°C(O)N(R°)$_2$; —NR°C(S)N(R°)$_2$; —NR°CO$_2$R°; —NR°NR°C(O)R°; —NR°NR°C(O)N(R°)$_2$; —NR°NR°CO$_2$R°; —C(O)C(O)R°; —C(O)CH$_2$C(O) R°; —CO$_2$R°; —OC(O)R°; —C(O)R°; —C(S)R°; —C(O)N(R°)$_2$; —OC(O)N(R°)$_2$; —C(NOR°)R°; —S(O)R°; —S(O)$_2$R°; —S(O)$_3$R°; —SO$_2$N(R°)$_2$; —NR°SO$_2$N(R°)$_2$; —NR°SO$_2$R°; —N(OR°)R°; —C(=S)N(R°)$_2$; —C(=NH)—N(R°)$_2$; or —(CH$_2$)$_{0-2}$ NHC(O)R° wherein each independent occurrence of R° is selected from hydrogen, C$_{1-6}$ aliphatic optionally substituted with NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(haloC$_{1-4}$ aliphatic), or haloC$_{1-4}$ aliphatic, wherein each of said C$_{1-4}$ aliphatic groups of R° is unsubstituted, an unsubstituted 5–6 membered heteroaryl or heterocyclic ring, phenyl, —O(Ph), or —CH$_2$(Ph), or two independent occurrences of R°, on the same substituent or different substituents, taken together with the atom(s) to which each R° group is bound, form a 3–8-membered cycloalkyl, heterocyclyl, aryl, or heteroaryl ring having 0–3 heteroatoms independently selected from nitrogen, oxygen, or sulfur.

8. The compound of claim 1, selected from:

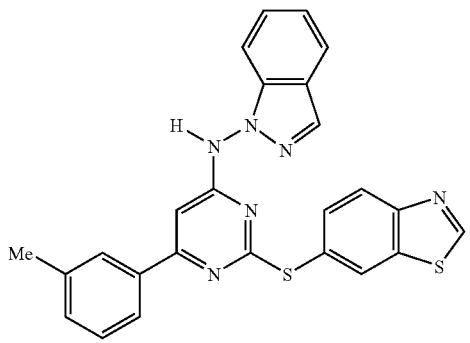

IIa-4

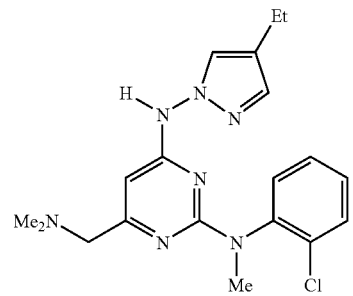

IIa-5

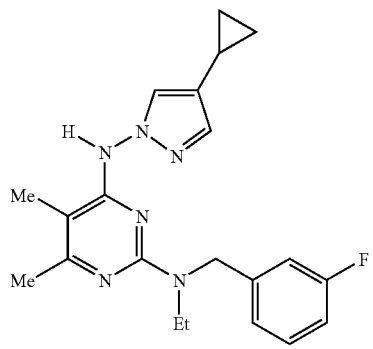

IIa-6

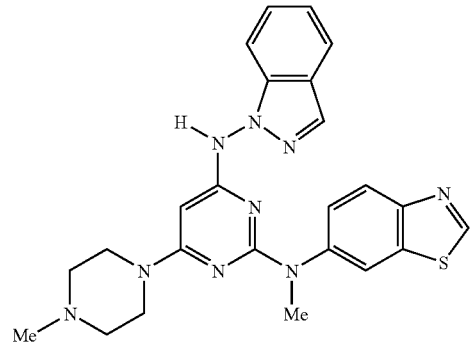

IIa-9

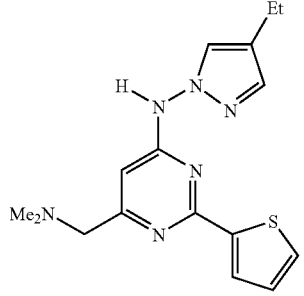

IIa-11

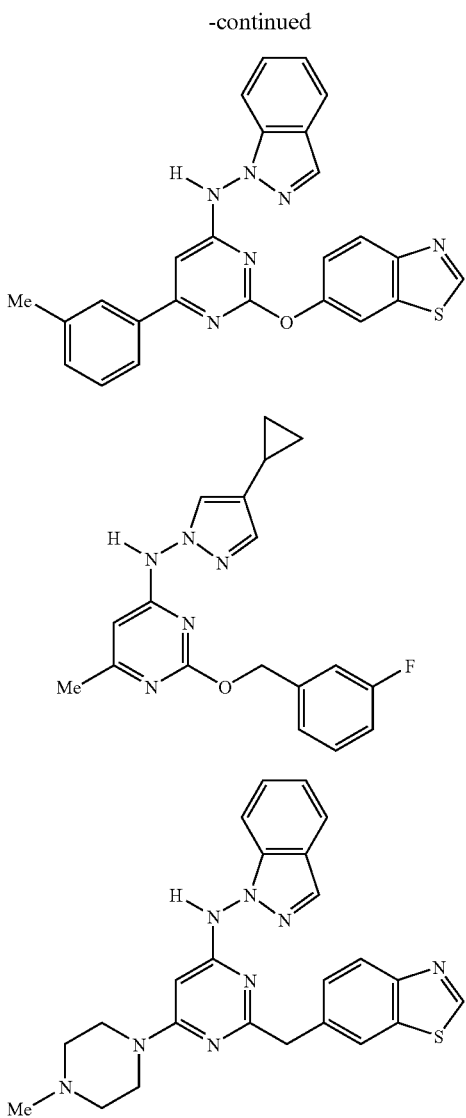

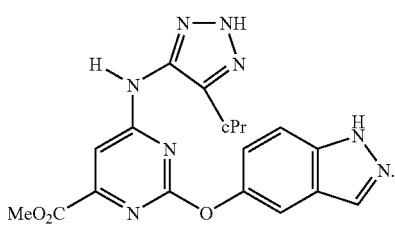

9. A composition comprising a compound according to claim 1 and a pharmaceutically acceptable carrier, adjuvant, or vehicle.

10. A composition comprising an effective amount of a compound of claim 1, and a pharmaceutically acceptable carrier, adjuvant, or vehicle.

11. The composition of claim 9, in an amount to detectably inhibit GSK-3, Aurora-2 or Src protein kinase activity.

12. The composition of claim 9, additionally comprising a therapeutic agent selected from a chemotherapeutic or anti-proliferative agent, an anti-inflammatory agent, an immunomodulatory or immunosuppressive agent a neurotrophic factor, an agent for treating cardiovascular disease, an agent for treating destructive bone disorders, an agent for treating liver disease, an anti-viral agent, an agent for treating blood disorders, an agent for treating diabetes, or an agent for treating immunodeficiency disorders.

13. A method for treating or lessening the severity of a colon cancer in a patient, comprising the step of administering to the patient a compound according to any one of claims 1, 2, 3–7 or 8.

14. A method for treating or lessening the severity of a colon cancer in a patient, comprising the step of administering to the patient a composition according to any one of claims 9–12.

* * * * *